United States Patent [19]
Wang et al.

[11] Patent Number: 5,997,900
[45] Date of Patent: Dec. 7, 1999

[54] ENCAPSULATION SYSTEM FOR THE IMMUNOISOLATION OF LIVING CELLS

[76] Inventors: Taylor G. Wang, 4999 Tyne Ridge Ct., Nashville, Tenn. 37220; Igor Lacik, Bystricka 34, 90201 Pezinok, Slovakia; Marcela Brissova, 1921 18th Ave. S., Nashville, Tenn. 37212; Amrutur V. Anikumar, 6925 Harpeth Glen Trace, Nashville, Tenn. 37221; Ales Prokop, 1032 Elmshade Ln., Nashville, Tenn. 37211; Alvin C. Powers, 6557 Cloverbrook Dr., Brentwood, Tenn. 37027

[21] Appl. No.: 08/843,468

[22] Filed: Apr. 16, 1997

Related U.S. Application Data

[60] Provisional application No. 60/015,593, Apr. 17, 1996, provisional application No. 60/015,791, Apr. 17, 1996, and provisional application No. 60/015,795, Apr. 17, 1996.

[51] Int. Cl.⁶ .................................................. A61K 9/50
[52] U.S. Cl. .......................................... 424/451; 424/455
[58] Field of Search ..................................... 424/491, 499, 424/451, 455

[56] References Cited

U.S. PATENT DOCUMENTS 5,011,634   4/1991   Pietsch et al. ............................ 264/47

FOREIGN PATENT DOCUMENTS 2034633   7/1992   Canada .

Primary Examiner—Peter F. Kulkosky
Attorney, Agent, or Firm—Benjamin Aaron Adler

[57] ABSTRACT

The present invention is drawn to a composition of matter comprising high viscosity sodium alginate, cellulose sulfate and a multi-component polycation. Additionally, the present invention provides methods for making capsules, measuring capsule permeability to immunologically-relevant proteins and treating disease in an animal using encapsulated cells.

Over one thousand combinations of polyanions and polycations were examined as polymer candidates suitable for encapsulation of living cells and thirty-three pairs were effective. The combination of sodium alginate, cellulose sulfate, poly(methylene-co-guanidine) hydrochloride, calcium chloride, and sodium chloride produced the most desirable results. Pancreatic islets encapsulated in this multicomponent capsule demonstrated glucose-stimulated insulin secretion in vitro and reversed diabetes without stimulating immune reaction in mice. The capsule formulation and system of the present invention allows independent adjustments of capsule size, wall thickness, mechanical strength and permeability, and offers distinct advantages for immunoisolating cells.

9 Claims, 15 Drawing Sheets

■ SA(HV), + CS, ● mixture of CS and SA(HV)

ENCAPSULATION SYSTEM FOR THE IMMUNOISOLATION OF LIVING CELLS

CROSS-REFERENCE TO RELATED APPLICATIONS

This application is a continuation of provisional patent application U.S. Ser. No. 60/015,593, filed Apr. 17, 1996, provisional patent application U.S. Ser. No. 60/015,791, filed Apr. 17, 1996, and provisional patent application U.S. Ser. No. 60/015,795, filed Apr. 17, 1996.

FEDERAL FUNDING LEGEND

This invention was produced in part using funds from the Federal government under grant no. NIH DK20593 and NASA contract NAS7-918. Accordingly, the Federal government has certain rights in this invention.

BACKGROUND OF THE INVENTION

1. Field of the Invention

The present invention relates generally to the fields of endocrinology, protein chemistry and biomedical engineering. More specifically, the present invention relates to a novel encapsulation system for the immunoisolation of living cells.

2. Description of the Related Art

Transplantation of cells to treat a variety of human diseases, such as diseases caused by hormone or protein deficiencies, is limited because transplanted cells are destroyed quickly by the recipient's immune system. To overcome this limitation, it is desirable that hormone- or protein-secreting cells be enclosed in a semi-permeable membrane that would protect cells from immune attack, while allowing the influx of molecules important for cell function/survival and efflux of the desired cellular products (see refs. 1–7).

The principle of immunoisolation or immunoprotection of cells for transplantation overcomes two main obstacles: 1) cell transplantation without the need for immunosuppression and its accompanying side effects, and 2) transplantation of cells from non-human species (xenograft) to overcome the limited supply of donor cells for such diseases as diabetes (refs. 8–12). Many diseases may be treated best by the regulated release of a cellular product (hormone, protein, neurotransmitter, etc.). Thus, a variety of cell types are candidates for transplantation of immunoisolated cells, including pancreatic islets, hepatocytes, neurons, parathyroid cells, and cells secreting various clotting factors.

One immunoisolation approach, encapsulation of pancreatic islets, is under investigation by a large number of groups and has been successful in reversing chemically-induced diabetes in rodents and in a small scale human clinical trial (refs. 1–3, 6, 13–17). Most cell encapsulation currently utilizes modifications of the procedure originated by Lim and Sun in which the encapsulant is suspended in a polyanionic aqueous solution and extruded by an air jet/syringe pump droplet generator into calcium ions (refs. 18 and 19). Poly(L-lysine), which is a cationic macromolecule, is then mixed with the hardened polyanionic gel, and a membrane is formed at the interface as a result of the ionic interaction. Because this is a binary system, however, all membrane parameters are tied to a single chemical complex. Attempts to optimize one parameter will affect all other parameters. The inability to adjust capsule parameters independently (for example, mechanical strength or permeability) has limited the success of this system (refs. 13 and 20). Capsules made with other binary polymer systems, such as Hydroxyethyl methacrylate/Methyl methacrylate (HEMA/MMA) suffer similar limitations (refs. 19, 21 and 22).

The prior art is deficient in the lack of effective means of encapsulating and immunoisolating living cells. The present invention fulfills this long-standing need and desire in the art.

SUMMARY OF THE INVENTION

To overcome the limitations of the prior art, the present invention provides a new multicomponent polymer capsule which allows for modification of individual capsule parameters such as capsule size, wall thickness, mechanical strength, permeability, and surface characteristics. The capsule characteristics can be adjusted and optimized for various, specific delivery systems, e.g., islet transplantation.

Over one thousand combinations of polyanions and polycations were examined as polymer candidates suitable for encapsulation of living cells. Thirty-three combinations were found to be useable. The combination of sodium alginate (SA), cellulose sulfate (CS), poly(methylene-co-guanidine)hydrochloride (PMCG), calcium chloride ($CaCl_2$), and sodium chloride (NaCl) produced the most desirable results.

Pancreatic islets encapsulated in this multicomponent capsule reversed diabetes in both strepzotocin-induced and non-obese diabetic (NOD) mice. Encapsulated rat islets demonstrated glucose-stimulated insulin secretion in vitro and reversed diabetes in vivo in mice. The capsule formulation and system of the present invention allows independent adjustments of capsule size, wall thickness, mechanical strength and permeability, and offers distinct advantages for immunoisolating cells.

In one aspect of the present invention, there is provided a composition of matter comprising high viscosity sodium alginate (SA-HV), cellulose sulfate, and a polycation. In a preferred embodiment of the present invention, the high viscosity sodium alginate and the cellulose sulfate are in a ratio of approximately 1:1. Further, a preferred embodiment includes the high viscosity sodium alginate and said cellulose sulfate at a total concentration of 0.8 wt-% to 2.4 wt-%. In a more preferred embodiment, the high viscosity sodium alginate and the cellulose sulfate are at a total concentration of 1.0 wt-% to 1.2 wt-%, in the ratio of 1:1.

In addition, an embodiment may be where the individual components of the polycation are at a concentration of 0.5 wt-% to 5.0 wt-%. A more preferred embodiment would include where each component of the polycation is at a concentration of 0.8 wt-% to 2.8 wt-%.

In addition, the present invention may include a polycation comprised of poly(methylene-co-guanidine) hydrochloride, calcium chloride and sodium chloride. In a most preferred embodiment, the poly(methylene-co-guanidine)hydrochloride is at a concentration of about 1.8 wt-%, the calcium chloride is at a concentration of about 1.0 wt-%, and the sodium chloride is at a concentration of about 0.9 wt-%.

Another aspect of the present invention includes a method of making capsules for the immunoisolation of cells comprising the steps of: providing a continuously-replenished polycation stream in a multiloop reactor; dropping uniformly-sized drops of anion solution and cells into said polycation stream; allowing said polycation stream to carry said drops, wherein said polycation and said anion react to form a capsule; collecting said capsules in a large excess of buffer; placing said capsules on a filter; and re-rinsing said capsules in buffer.

In yet another aspect of the present invention, there is provided a method for measuring capsule permeability to immunologically-relevant proteins, comprising the steps of: encapsulating an antibody and an appropriate carrier in a capsule formulation to be tested; equilibrating said capsule and encapsulated antibody in a buffer; adding labeled said immunologically-relevant proteins to said buffer; and measuring an amount of said immunologically-relevant proteins which entered said capsule. In a preferred embodiment, the carrier is protein A-sepharose, and the immunologically relevant protein is an immunoglobulin.

In an additional aspect of the present invention, there is provided a method of treating disease in an animal, comprising the steps of: encapsulating cells, that secrete a protein or hormone that ameliorates said disease, in a capsule, wherein said capsule is comprised of high viscosity sodium alginate, cellulose sulfate, and a polycation; and transplanting said encapsulated cells into said animal, wherein said transplated encapsulated cells secrete said protein or hormone. A particular embodiment of this aspect of the invention is drawn to treating diabetes using pancreatic islet cells. Such cells may be encapsulated in a capsule wherein the high viscosity sodium alginate and the cellulose sulfate are at a total concentration of 1.0% wt-% to 1.2 wt-% and in a ratio of approximately 1:1, and the polycation is comprised of poly(methylene-co-guanidine)hydrochloride at a concentration of about 1.8 wt-%, the calcium chloride is at a concentration of about 1.0 wt-%, and the sodium chloride is at a concentration of about 0.9 wt-%.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the capsule prepared in the absence of sodium chloride; CS 0.6 wt-%/SA 0.6 wt-%, 0.6 wt % PMCG, and 0.5 wt % $CaCl_2$. The reaction time was 90 seconds.

FIG. 3 shows the capsule prepared in the presence of sodium chloride; CS 0.6 wt-%/SA 0.6 wt-%, 0.6 wt % PMCG, 0.5 wt % $CaCl_2$, and 0.9 wt % NaCl. The reaction time was 90 seconds.

FIG. 4 shows the capsules prepared by the complexation reaction.

FIG. 10 shows the biocompatibility of empty capsules. The two capsules shown were prepared under identical processing steps, but were different in PMCG concentration (right panel-1.8% PMCG; left panel-1.0% PMCG) and were transplanted intraperitoneally into normal C57/B16 mice. Capsules were retrieved 30 days later and photographed.

FIG. 11 shows that the transplantation of encapsulated rat islets reverses diabetes.

FIG. 12 shows that the encapsulated islets have long-term function and biocompatibility.

DETAILED DESCRIPTION OF THE INVENTION

Figure 1:
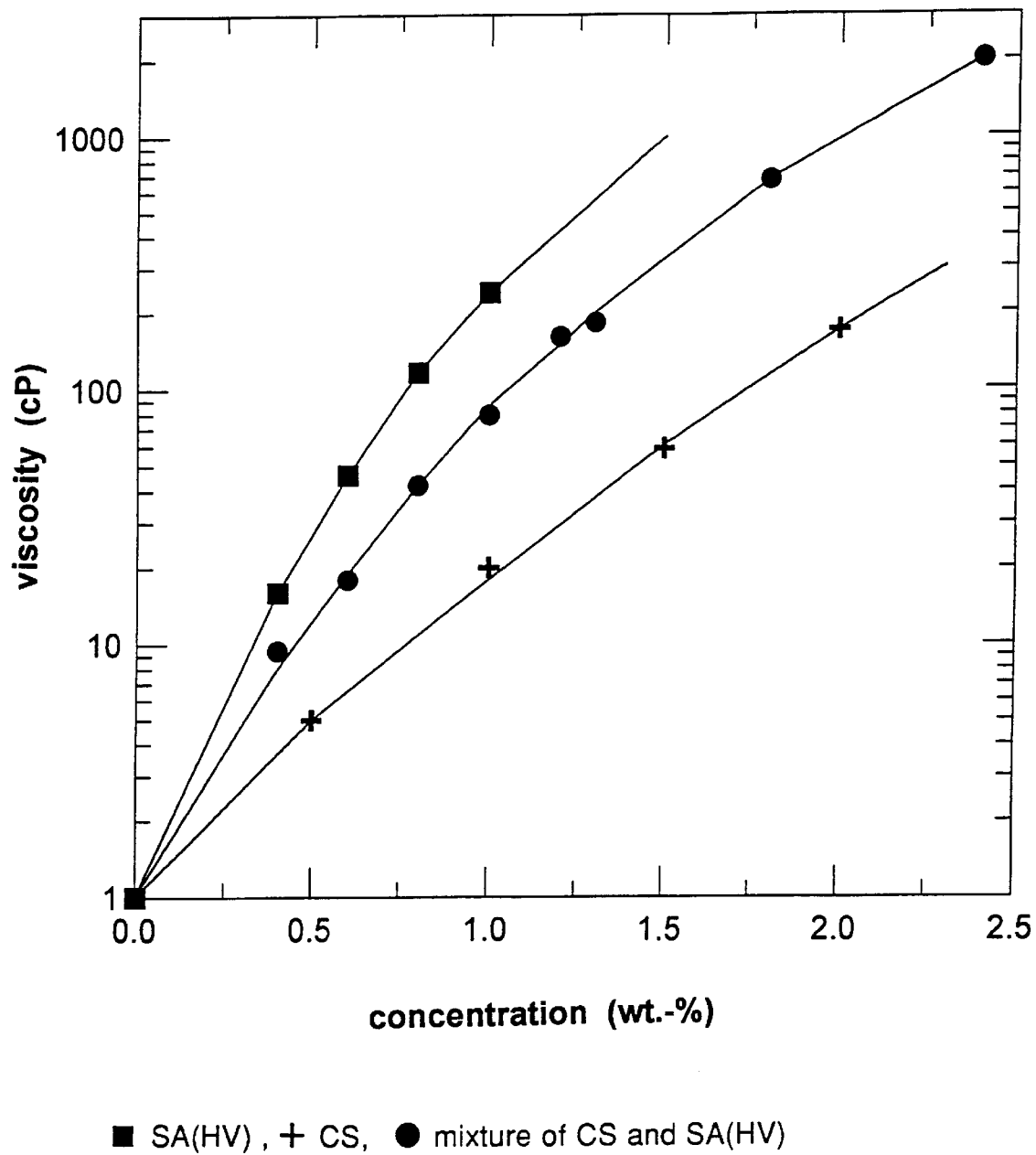
FIG. 1 shows viscosity as a function of polyanion concentration in phosphobuffered saline (PBS) at 21° C. SA(HV) (filled square); CS,+; mixture of CS and SA(HV) in the ratio of 1:1, filled circle.

In the description of the present invention, a following abbreviations may be used: SEC, size exclusion chromatography; SA=sodium alginate; CS, cellulose sulfate; PMCG, poly(methylene-co-guanidine); PAS, protein A sepharose; PSD, pore size distribution; PBS, phosphate-buffered saline; HBSS, Hank's Balanced Saline Solution; IBMX, 3-isobutyl-1-methyl-Xanthine.

The present invention is directed to a compositions of matter comprising various anion and polycation mixtures. A particularly workable combination is that of high viscosity sodium alginate, cellulose sulfate and a multicomponent polycation.

It is specifically contemplated that pharmaceutical compositions may be prepared using protein-secreting cells encapsulated in the novel capsules of the present invention. In such a case, the pharmaceutical composition may comprise the cells and a pharmaceutically acceptable matrix. A person having ordinary skill in this art readily would be able to determine, without undue experimentation, the appropriate cell number, matrix composition and routes of administration of the capsule of the present invention.

Additionally, the present invention provides methods for making capsules, measuring capsule permeability to immunologically-relevant proteins and treating disease in an animal using encapsulated cells.

Immunoisolation is based on the premise that a membrane can protect secreting cells, such as pancreatic islets, from the host immune system and yet allow entrance and exit of substances required for cell maintenance and stimulation of protein of hormone secretion. Although the concept of immunoisolation is straightforward, stringent biologic and physical criteria must be met for long-term survival and function of the immunoisolated cell within a biologic host. Immunoisolation devices must be biocompatible with the host and with the transplanted cell and must allow entry of oxygen and nutrient molecules required for health of the enclosed cell. The promise of immunoisolation has lead to the development of a wide array of devices including microcapsules, macrocapsules, hollow fibers, tubular membranes, intravascular devices, and flat sandwich pouches. Encapsulation of cells within microcapsules has been most widely-used, but difficulties with capsule biocompatibility, capsule strength, and the inability to define and modify parameters critical for immunoisolation and cell survival has prevented this technology from achieving its full potential.

Using a new combination of polymers and new encapsulation technology, the present invention provides a multicomponent capsule formed by polyelectrolyte complexation. This complexation has been evaluated in vitro and in vivo. This new capsule and encapsulation technology allows for a systematic modification of capsule size, membrane thickness, mechanical strength, membrane permeability, and surface characteristics based on feedback from biological results in vitro and in vivo.

The following examples are given for the purpose of illustrating various embodiments of the invention and are not meant to limit the present invention in any fashion.

EXAMPLE 1
Assessment of Capsule Permeability

To assess capsule permeability to immunologically-relevant proteins like IgG, protein A-sepharose (PAS, Sigma Chemicals, St. Louis, Mo.) was encapsulated. Empty capsules and capsules containing ~18 $\mu$l of packed PAS were equilibrated in phosphate-buffered saline (PBS) with 0.2% Tween 20 and 0.2% bovine serum albumin. Iodinated IgG (approximately 10,000 cpm; New England Nuclear, Wilmington, Del.) was added to the PBS and aliquots of PAS were removed at selected time points over 24 hours. After removal at each time point, the encapsulated PAS was washed five times with 4 ml of PBS. The amount of IgG that had entered the capsule was quantitated in a gamma counter. Unencapsulated or free PAS served as a positive control. This method of permeability assessment can be adapted for measuring entry of almost any protein since the only requirements are an antibody against the protein of interest—in such a case, the PAS would be preincubated with the antibody before encapsulation—and the ability to radiolabel the protein.

EXAMPLE 2
Assessment of Insulin Secretion

Insulin secretion by encapsulated rat islets was evaluated in a cell perifusion apparatus with a flow rate of 1 ml/minute with RPMI 1640 with 0.1% BSA as a perifusate. Encapsulated islets were perifused with 2 mM glucose for 30 minutes and the column flowthrough discarded. Fractions of perifusate were collected at three-minute intervals during a 30 minute perifusion of 2 mM glucose, a 30 minute perifusion of 20 mM glucose+0.045 mM IBMX, and a 60 minute perifusion of 2 mM glucose. Samples were assayed in duplicate for insulin using Coat-a-Count kits (Diagnostic Products Corporation, Los Angeles, Calif.) with a rat insulin standard. The amount of insulin secreted was normalized for the number of islets.

EXAMPLE 3
Animal Studies

Pancreatic islets were isolated from male Sprague-Dawley rats (250–275 g, Harlan). Briefly, the pancreatic duct was inflated with a solution of Hank's Balanced Saline Solution (HBSS) containing collagenase (Boehringer-Mannheim, Collagenase P). Groups of 3 pancreases were digested in 2 mg collagenase/pancreas in HBSS for 6–13 minutes at 37° C. using a wrist-action shaker. The digestion was stopped by the addition of cold HBSS with 10% Newborn Calf Serum and shaken vigorously for 10–15 seconds. The digested material was washed three times with cold HBSS and filtered through a wire mesh cell strainer to remove undigested material. Pancreatic islets were separated using a Histopaque-1077 gradient and stored in University of Wisconsin storage solution ("Viaspan") for 19–24 hours before encapsulation.

Encapsulated rat islets were transplanted into the peritoneal cavity of diabetic mice (either strepzotocin-induced or NOD mice). Diabetes was induced in normal C57/B16 mice by the intraperitoneal injection of strepzotocin (200 mg/kg) 3–7 days prior to transplantation of encapsulated islets. NOD mice were purchased from Taconic Laboratories (Germantown, N.Y.) and bred in microisolator cages with autoclaved bedding and water. Between 18–24 weeks of age, 50–75% of females from this colony became diabetic. When diabetes was present for 2–4 weeks, female NOD mice received a transplantation of encapsulated islets. Approximately 1000 encapsulated rat islets (0.8 mm capsule with 0.1 mm wall thickness and an exclusion limit of 230 kDa) in a packed capsule volume of 0.2–0.5 ml were sterilely transplanted intraperitoneally into metofane-anesthetized mice. The blood sugar of the mice was measured using a One-touch glucometer using blood obtained from the retroorbital plexus or a tail vein.

EXAMPLE 4

Capsule Development: Polymer Screening

To develop new capsule formulations, over one thousand combinations of water-soluble polyanions and polycations were tested. A droplet of each polyanion (3–5 mm diameter) was manually dropped into a beaker of polycation solution. Formation of a capsule was noted by visual observation under a microscope. A crude estimate of mechanical stability of the capsule was obtained by manual compression of capsules. For those pairs that showed promise in the screening tests, the effects of pH, molecular weight of the polymer, and charge density on capsule formation were examined (data not shown). Polymer pairs that formed capsules were also tested for biocompatibility using an in vitro culture system with rat insulinoma cells (RIN 1046-38 cells from American Tissue Culture Collection, Rockville, Md.). The growth rate of RIN cells, cultured in the presence of either a solution or a membrane of the polymer of interest, was used to select polymers for further investigation. Twenty-one multicomponent membrane systems were studied (TABLE I). A combination of sodium alginate (SA), cellulose sulfate (CS), polymethylene-co-guanidine (PMCG), $CaCl_2$, and NaCl was found to be most effective.

TABLE I

Results ot the Screening of Multicomponent Membrane Systems.

| Polyanion Blend | Polycation Blend |
| --- | --- |
| HV Alginate/Cellulose Sulfate | Polymethylene-co-Guanidine/Calcium Chloride |
| HV Alginate/Cellulose Sulfate | Polydimethylamine-co-epichlorhydrin-modified quaternary |
| HV Alginate/Cellulose Sulfate | Polyvinylamine/Calcium Chloride |
| HV Alginate/Cellulose Sulfate | Polylysine/Calcium Chloride |
| HV Alginate/Cellulose Sulfate | Polyvinylamine(LMW & HMW) |
| Alginate/Cellulose Sulfate/ Collagen | Polymethylene-co-guanidine/Calcium Chloride |
| Alginate/Carrageenan kappa/ LTM-Agarose | Protamine/Calcium and Potassium Chloride |
| Alginate/Carrageenan kappa and lambda | Protamine/Calcium and Potassium Chloride |
| Alginate/Carrageenan kappa | Protamine/Calcium and Potassium Chloride |
| Alginate/Cellulose Sulfate | Spermine/Polydimethylamine-co-guanidine |
| Alginate | Spermine/Polydimethylamine-co-guanidine |
| Alginate/LTM Agarose | Polybrene/Calcium Chloride |
| HV Alginate/Gellan | Protamine/Calcium and Potassium Chloride |
| HV Alginate/Gellan | Lysozyme/Calcium Chloride |
| Carrageenan kappa and iota | Protamine/Calcium and Potassium Chloride |
| Carrageenan kappa/ Hyaluronic Acid | Protamine/Calcium and Potassium Chloride |
| Carrageenan kappa/ Hyaluronic Acid | Polybrene |
| Carrageenan kappa/ Chondroitin Sulfate A | Polyvinylamine(LMW & HMW) |

TABLE I-continued

Results ot the Screening of Multicomponent Membrane Systems.

| Polyanion Blend | Polycation Blend |
| --- | --- |
| LE-Pectin/Cellulose Sulfate | Polymethylene-co-guanidine/Calcium Chloride |
| LE-Pectin/Cellulose Sulfate | Quart-Polyamine/Calcium Chloride |
| LE-Pectin | Quart-Polyamine/Calcium Chloride |
| LE-Pectin/LTM-Agarose | Poybrene/Calcium Chloride |
| Xanthan | Polylysine/Spermine |
| Xanthan | Polylysine/Polyallylamine |
| Xanthan/Alginate | Polymethylene-co-guanidine |
| Xanthan/Cellulose Sulfate | Polymethylene-co-guanidine |
| Xanthan | Polyvinylamine/Polyethyleneimine-hydroxyethylated |
| Carboxymethylcellulose (HMW)/Cellulose Sulfate | Chitosan(LMW)/Polyvinylamine |
| CMC(HMW)/Hyaluronic Acid | Chitosan(LMW)/Polyethyleneimine-hydroxylethylated |
| CMC(HMW)/Hyaluronic Acid | Chitosan(LMW)/pDADMAC |
| CMC(HMW)/Hyaluronic Acid | Chitosan(LMW)/Quaternary-Polyamine |
| CMC(HMW)/Hyaluronic Acid | Chitosan(LMW)/Polydimethylamine-co-epichlorhydrin modified Quaternary |
| CMC(HMW)/Carrageenan lambda | Polymethylene-co-guaridine |

LE: Low Esterified,
LTM: Low Temperature Melting,
MMW: Medium Molecular Weight,
LMW: Low Molecular Weight,
HMW: High Molecular Weight,
HV: High Viscosity

EXAMPLE 5

Capsule Processing

Capsules may be made in a chemical reaction chamber. A multi-loop chamber reactor filled with cation solution is particularly advantageous. The cation solution bath was fed by a cation stream which continuously replenished the solution and carried away the anion drops being introduced into the chamber. SA/CS droplets, with pancreatic islets enclosed, entered the $PMCG/CaCl_2/NaCl$ stream at an oblique angle, so as to minimize the islet decentering and drop deformation problem associated with impact (refs. 24–28). The droplets were then carried into the multi-loop reactor by the polycation stream. The reactor used must allow for adjustment of reaction time and negate gravitational effects. These features facilitate tight control of capsule sphericity, membrane thickness and uniformity. Using such a reactor, one can produce capsules with diameters from 0.5 mm to 3.0 mm and membrane thicknesses from 0.006 mm to 0.125 mm.

EXAMPLE 6

Chemicals

The polymers used were: high viscosity sodium alginate (SA-HV) from Kelco (San Diego, Calif.), cellulose sulfate, sodium salt (CS) from Janssen Chimica (Geel, Belgium), poly(methylene-co-guanidine)hydrochloride (PMCG) from Scientific Polymer Products Inc. (Ontario, N.Y.), dextran sulfate from Sigma (St. Louis, Mo.) and low viscosity sodium alginate (SA-LV) from Kelco (San Diego, Calif.). Streptozotocin (STZ) was purchased from Sigma (St. Louis, Mo.), collagenase P from Boehringer-Mannheim (Indianapolis, Ind.) and phosphate buffered saline (PBS) from Gibco (catalogue #21600-069). All salts were reagent grade from Fisher or Aldrich.

High viscosity sodium alginate is a product isolated from the seaweed *Macrocystis Pyrifera*. According to information provided by the manufacturer, it consists of 40.6% of mannuronic acid blocks, 17.7% of guluronic acid blocks and the rest is the alternating copolymer of mannuronic and guluronic units (ref. 29). The average number of guluronic units forming the blocks is 6.0 (ref. 30). The average molecular weight of SA-HV equal to $4.6 \times 10^5$ was determined by viscosimetry. The measurement was done in 0.1 M aqueous NaCl at 20° C. by using Mark-Houwink parameters a=1.00 and $K=2.0 \times 10^{31\ 3}$ cm³/g according to work of SmidsrØd (ref. 30). These parameters were used for sodium alginate isolated from *Macrocystis pyrifera* although they were found for sodium alginate isolated from *Laminaria digitata* (ref. 31). However, as shown by Martinsen et al., the composition characteristics of this alginate and that isolated from *Macrocystis pyrifera* are almost identical; hence, one can assume they both have the same solution properties (ref. 30). The viscosity of SA-HV in phosphate-buffered saline solution (PBS) as a function of concentration at 21° C. is given in FIG. 1.

For cellulose sulfate, sodium salt, it was determined that the viscosity average molecular weight of CS was equal to $1.2 \times 10^6$. Measurements were performed in 0.5 M aqueous NaCl solution at 25° C., and Mark-Houwink parameters $K=6.37 \times 10^{-4}$ cm³/g and a=0.94 from Kishino et al. were used (ref. 32). The degree of sulfation (DS) obtained by elemental analysis (Microlab, Norcross, Ga.) was equal to 2.6 (19.6 wt.-% of sulfur). The viscosity of a semidilute solution of CS in PBS as a function of concentration is shown in FIG. 1 which also depicts the viscosity/concentration dependence of SA-HV/CS mixture in PBS (weight ratio 1:1).

Poly(methylene-co-guanidine)hydrochloride is a product of a polycondensation reaction of guanidine (or cyanoguanidine) with formaldehyde and ammonium chloride (ref. 33). The molecular weight, provided by the manufacturer, is 5000. It is supplied as a concentrated (35–50wt.-%) solution in water. Residual formaldehyde was removed by a freeze-drying technique followed by drying in vacuum at 50° C. for 48 hours. Based on the results from elemental analysis (Microlab, Norcross, Ga.), the amount of nitrogen, incorporated in both amine and imine groups, is 50–60 mole-% which determines high basicity of this compound.

EXAMPLE 7

Individual Role of the Components on the Capsule Formation Process

TABLE II comprises the summary of the membrane formation process when a compound (or compounds) of the same charge are combined with the compound (or compounds) of the opposite charge. This experiment illustrates how the individual components affect the capsule formation process and the final properties of the capsule. The effect of NaCl is shown separately. Properties at three successive stages of the capsule processing are described: 1) after collection of the polyanion drops and the first wash in PBS, 2) after capsule treatment in citrate, and 3) after storage in PBS.

Experiments 1–4 in TABLE II describe the interactions of SA-HV with $CaCl_2$ and PMCG as well as when these cation compounds are used either as a mixture or individually in two successive reaction steps. Experiment 1 represents the classical $SA/CaCl_2$ bead formation. Note when the calcium ions are removed by sodium citrate treatment, the capsules dissolved. Capsules formed in Experiment 2 ruptured shortly after their preparation and storage in PBS. Stable, yet rather swollen and fragile capsules resulted from Experiments 3 and 4.

Experiments 5 to 8 in TABLE II reveal the reactivity of CS toward the counterions at the same conditions as in the experiments for SA-HV. Reaction with $CaCl_2$ (Experiment 5) gave a precipitate which dissolves slowly in PBS, and rapidly in the sodium citrate solution. Soft, shrunk and stable capsules were obtained by reaction of CS with PMCG (Experiment 6). When the solution of the $PMCG/CaCl_2$ mixture was used in a single step reaction (Experiment 7), the capsules obtained were soft and stable and possessed a fine sponge-like structure. The capsules formed in Experiment 8 were made following the procedure in Experiment 5, but, due to instability of $CS/CaCl_2$

TABLE II

Summary of Capsule formation process and role of individual components.

| Expt | SA-HV 1 wt.-% PBS | CS 1 wt.-% PBS | $CaCl_2$ 1 wt.-% $H_2O$ | PMCG 1 wt.-% 0.9% NaCl pH 7.5 | First wash in PBS | 50 mM Sodium citrate (5 min) | Storage in PBS (24 hrs) |
|---|---|---|---|---|---|---|---|
| 1 | / | — | / | — | T, beads slowly dissolved | quickly dissolved | — |
| 2 | / | — | — | / | partially shrunk | — | swelling, ruptured |
| 3[b] | / | — | / | / | beads | swelling | T, swollen, stable, fragile |
| 4[c] | / | — | / | / | beads | swelling | T, swollen, stable, fragile |
| 5 | — | / | / | — | shrunk, slowly dissolved | quickly dissolved | — |
| 6 | — | / | — | / | shrunk, stable | — | NT, shrunk, stable |
| 7[b] | — | / | / | / | shrunk, stable | shrunk, stable | ST, shrunk, stable, fine sponge-like |
| 8[c] | — | / | / | / | shrunk, stable | shrunk, stable | NT, shrunk, stable, coarse sponge-like |
| 9[a] | / | / | / | — | beads, slowly dissolved | quickly dissolved | — |
| 10[a] | / | / | — | / | irregular shape | — | swelling, ruptured |

TABLE II-continued

Summary of Capsule formation process and role of individual components.

| Expt | SA-HV 1 wt.-% PBS | CS 1 wt.-% PBS | CaCl$_2$ 1 wt.-% H$_2$O | PMCG 1 wt.-% 0.9% NaCl pH 7.5 | First wash in PBS | 50 mM Sodium citrate (5 min) | Storage in PBS (24 hrs) |
|---|---|---|---|---|---|---|---|
| 11[a,b] | / | / | / | / | ST beads | ST capsules, stable | ST, strong, stable, visible ST membrane |
| 12[a,c] | / | / | / | / | ST beads | ST capsules, stable | ST, strong, stable, visible membrane, precipitated core |

T, ST, NT - transparent, semitransparent, nontransparent
[a]SA-HV/CS mixture contained 1 wt.-% SA-HV and 1 wt.-% CS in PBS
[b]PMCG/CaCl$_2$ mixture contained 1 wt.-% PMCG, 1 wt.-% CaCl$_2$ in 0.9 wt.-% NaCl at pH 7.5
[c]PMCG reaction is a second step following the bead formation using CaCl$_2$ in the first step complex in PBS, instead of being washed in PBS they were drained from CaCl$_2$ solution and transferred directly into PMCG. The resulting capsules showed a coarse sponge-like structure.

Finally, the third group of experiments, experiments 9 to 12 in TABLE II, represent the situation when both polyanion components, SA-HV and CS, participate in the capsule formation process. The SA-HV/CS/CaCl$_2$ beads (Experiment 9) showed a slightly lower transparency than those obtained in Experiment 1 (SA/Ca), but were more transparent than CS/CaCl$_2$ beads from Experiment 5. Similarly, as in Experiment 2, capsules formed in Experiment 10 were unstable in PBS. In Experiment 11, the mixture of SA-HV/CS was interacted in a single step process with the PMCG/CaCl$_2$ mixture. In this case, the capsules were spherical, stable, strong, semitransparent, and exhibited a distinct membrane. When the capsule formation procedure was divided into two steps so that PMCG reacted with pre-formed SA-HV/CS/CaCl$_2$ beads (Experiment 12), the resulting capsules were weaker than those made in Experiment 11, and their membrane was thinner and less transparent. The capsule core is more opaque than that in Experiment 11 and, after a short time, a precipitate is seen in the capsule core.

The results in TABLE II led to a study of the polyelectrolyte system represented by Experiment 11: capsule formation based on the principle of a single step interaction of SA-HV/CS mixture with polycation mixture. By varying the overall concentration of the polyanion mixture ranging from 0.8 wt.-% to 2.4 wt.-% at a different relative component ratio, the optimum composition and concentration of the polyanion solution has been determined. The optimum weight ratio CS/(SA-HV+CS) was found to be approximately 0.5. Augmentation in CS content showed a negative impact on capsule sphericity, smoothness and transparency. On the other hand, capsules prepared at low CS/(SA-HV+CS) ratio were less mechanically strong. A preferred capsule shape was achieved at the minimal total polyanion concentration 1.0 wt.-% and a capsule of preferred strength was obtained when the total polyanion concentration was at 1.2 wt.-%. The studies described below utilized the single-step interaction of the polycation mixture with the mixture of polyanions where SA-HV:CS was 1:1.

The attributes of the polycation solution are closely bound with other variables such as concentration and composition of the polyanion solution, capsule size, and reaction time. Composition of cation solution was tested over a large concentration range of all components with the reaction time varying from a few seconds to several minutes. An increased ratio of PMCG/CaCl$_2$ results in the capsules with lower transparency, a thicker membrane and higher mechanical strength. Moreover, the complexation reaction of these two cation compounds with a given polyanion matrix is significantly influenced by the presence of sodium chloride, as demonstrated below.

EXAMPLE 8

Effect of NaCl

Figure 2A:
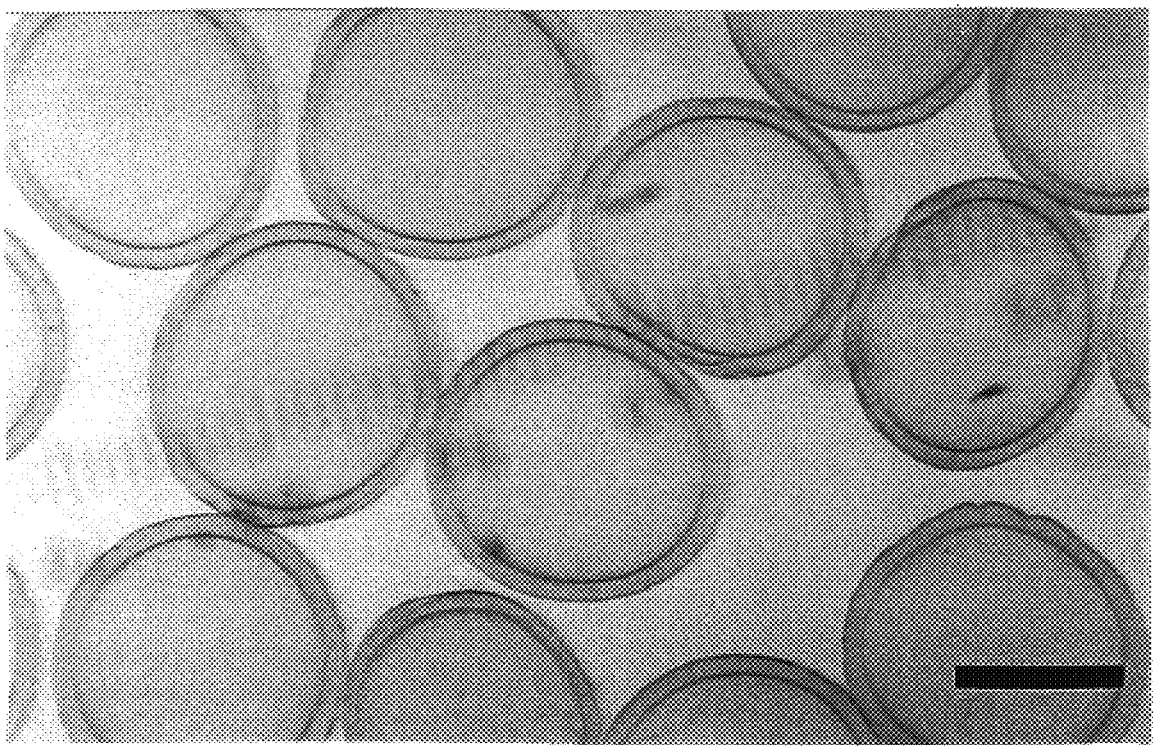
FIG. 2A: results after the first wash.
Figure 2B:
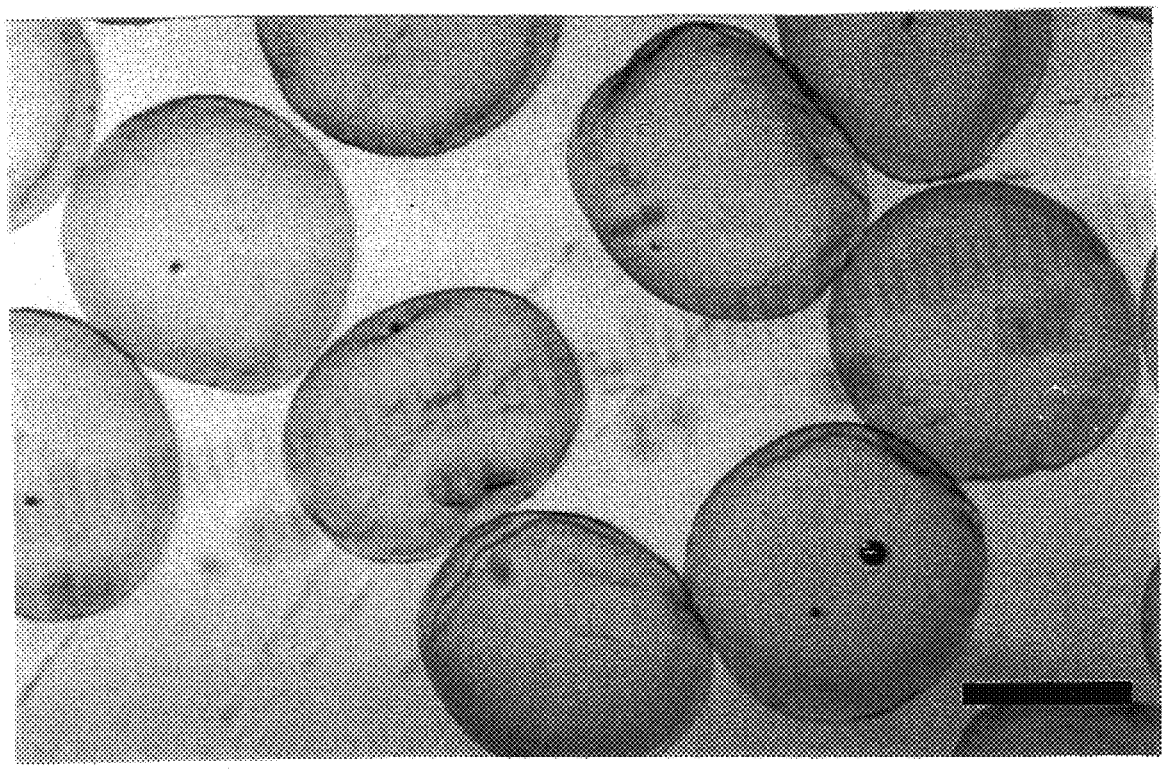
FIG. 2B: results after storage in PBS. The bar is 0.5 mm.
Figure 3A:
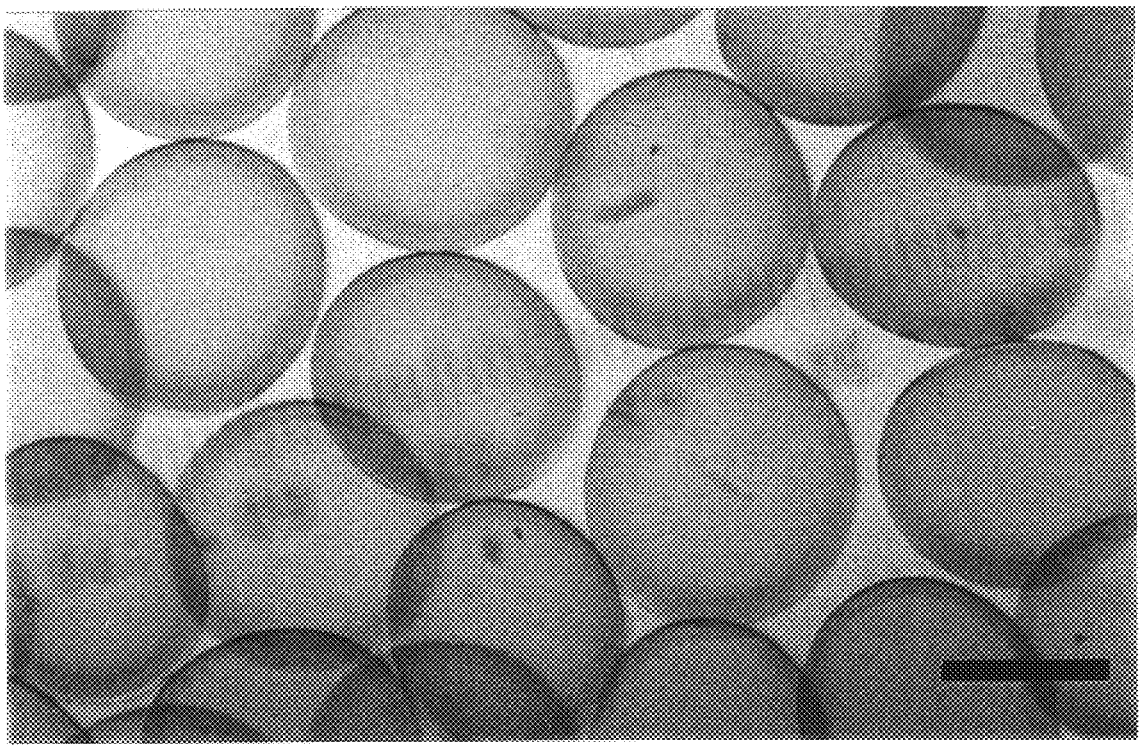
FIG. 3A: results after the first wash.
Figure 3B:
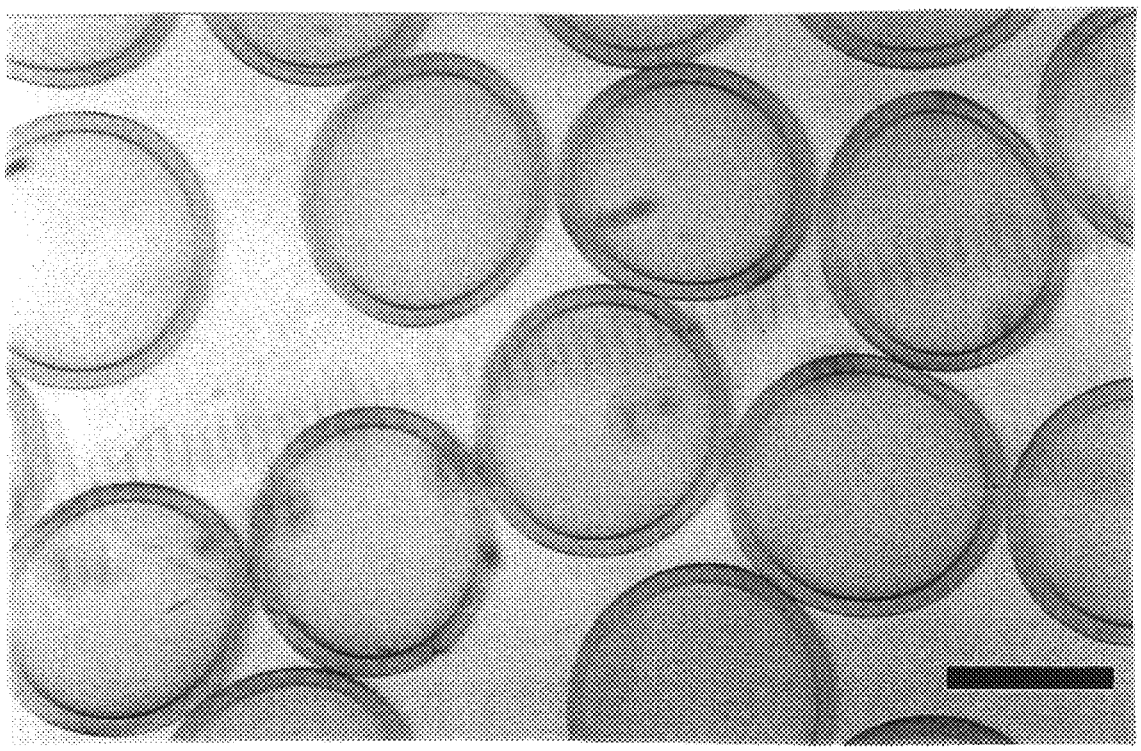
FIG. 3B: results after storage in PBS. The bar is 0.5 mm.

FIG. 2 shows capsules after a first wash and after storage in PBS following the citrate treatment, respectively. In this case, the cation solution did not contain sodium chloride. Capsule deformation seen at the first stage of the process is transferred into the quality of the membrane at the final stage where membrane defects are strongly apparent as ridges and wrinkles (FIG. 2A). On the other hand, much higher capsule quality is obtained at both stages of capsule formation when sodium chloride is present in cation solution (FIG. 3). The membrane is smooth and free of defects. Note that under these conditions the membrane is clearly visible only after calcium removal.

EXAMPLE 9

Capsule formation

Figure 4A:
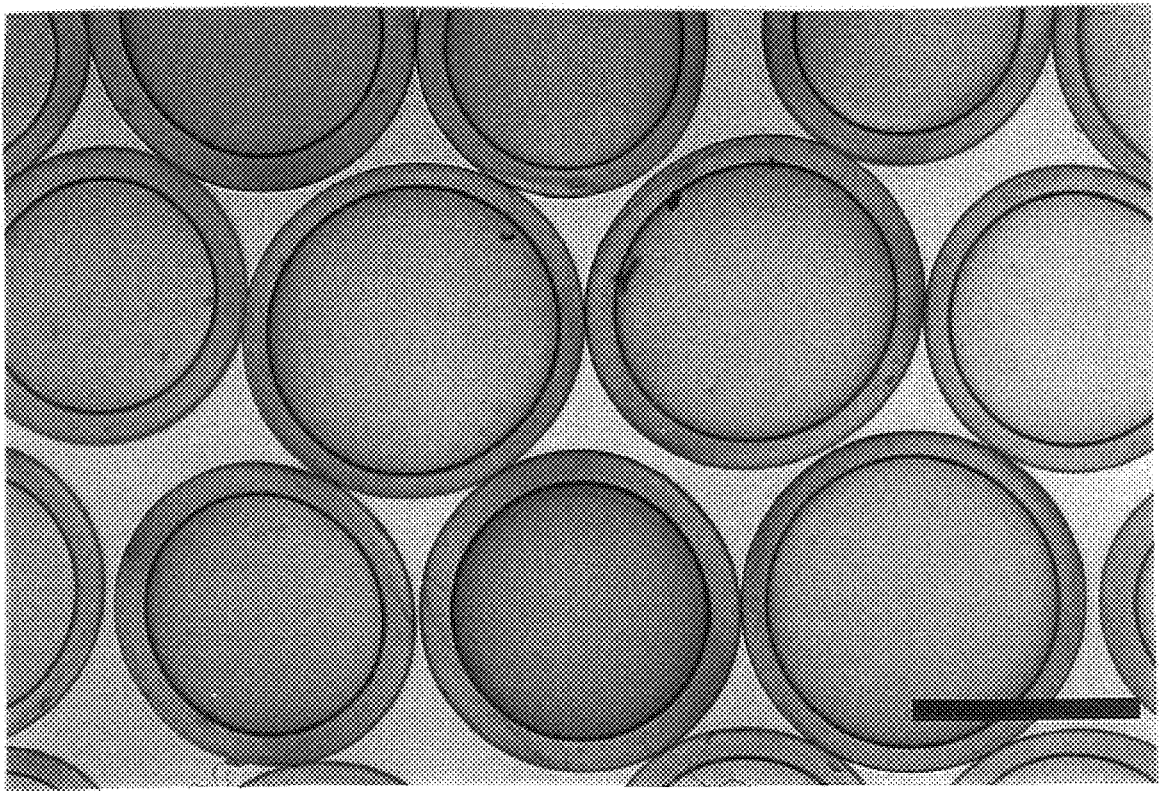
FIG. 4A: capsules prepared in a beaker, with a reaction time of 30 seconds and a collection time of 30 seconds.

FIG. 4 compares the capsules prepared by two different techniques. In the first case (FIG. 4A), capsules were collected for 30 seconds in a beaker containing polycation solution and then were left to react with the polycation for another 30 seconds (the average reaction time for the entire batch was 45 seconds). This represents the preferred conditions for preparing a large batch of capsules, which involves changing the collecting cation solution every 30 seconds followed by the washing step.

Figure 4B:
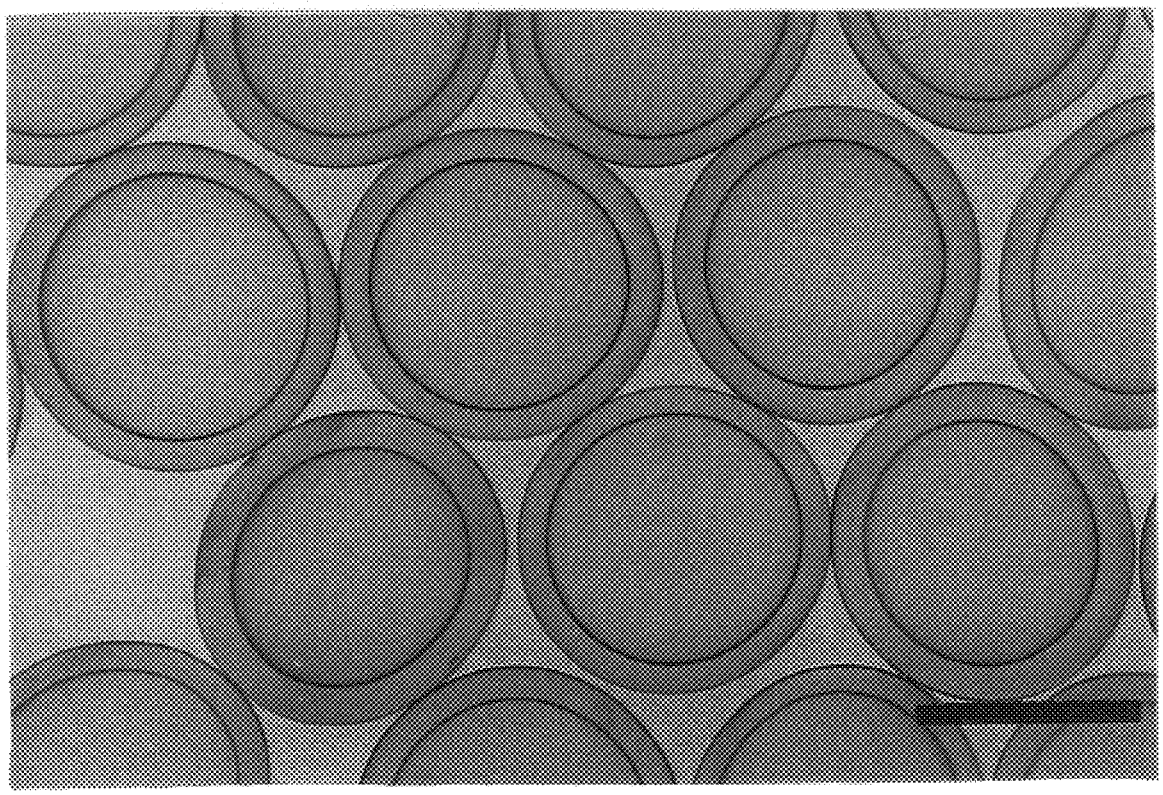
FIG. 4B: capsules prepared in the chemical reactor, with a reaction time of 45 seconds. The bar is 0.5 mm.

In the second case, the capsules were continuously produced in the chemical reactor, with the residence time of each capsule being 45 seconds. The capsules were collected for 60 seconds in a large excess of PBS. After collection, they were washed on a screen to remove any residual polycation and transferred to fresh PBS. Capsules shown in FIG. 4A exhibit much higher polydispersity in size and membrane thickness than those prepared by using the reactor (FIG. 4B). For these experiments, the total concentration of polyanion solution was 1.2 wt.-% and the cation solution contained 1.8 wt.-% PMCG, 1.0 wt.-% CaCl$_2$ and 0.9 wt.-% NaCl at pH 7.5.

EXAMPLE 10

Capsule Size and Membrane Thickness

Figure 5:
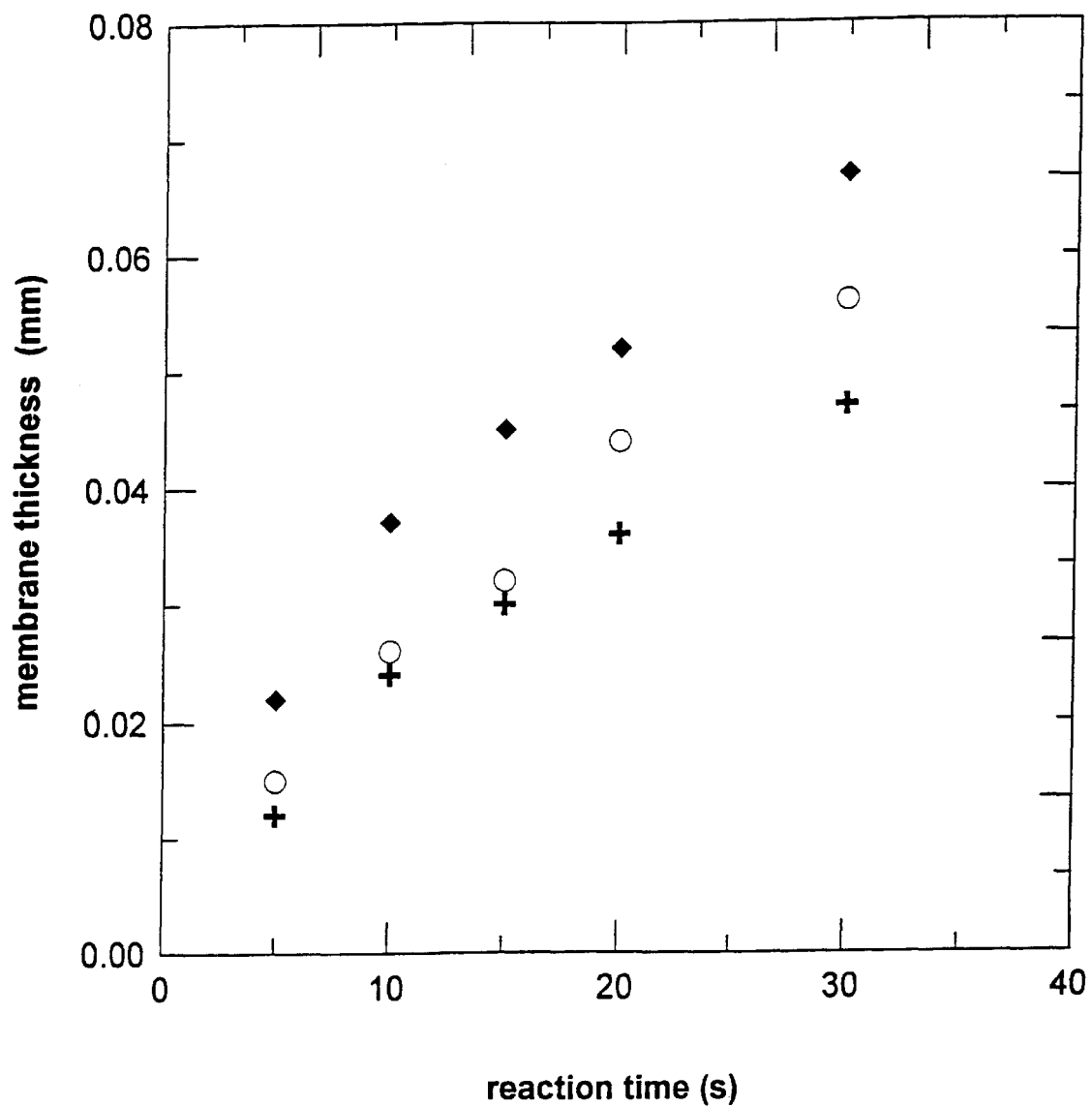
FIG. 5 shows the membrane thickness at different stages of capsule processing. See TABLE III for the conditions of capsule preparation: after first wash in PBS, ◊; after citrate treatment, open circle; after 24 hrs in PBS,+.

The results on the measurements of capsule size and membrane thickness at the different stages of capsule formation are listed in TABLE III and FIG. 5. The data on the membrane thickness were not optically corrected, and the measurements of capsule diameter were accurate within 3%. These parameters were examined as a function of reaction time at the overall polyanion concentration 1.2 wt.-%.

Since the polyanion drop size was kept constant throughout the experiment, the data in TABLE III show the effect of reaction time on the swelling of capsules at the initial stage of preparation (after the first wash with PBS). Above a certain reaction time, the network density becomes high enough to prevent the capsule from swelling; consequently the capsule size does not change. Concerning the next stages of capsule processing, the capsules prepared at shorter reaction times (less than 30 seconds) gradually

TABLE III

Capsule size at different stages of capsule processing.

| Time (s) | Capsule size (mm) | | |
|---|---|---|---|
| | First wash in PBS | Sodium citrate (5 min) | Storage in PBS (24 hrs) |
| 5 | 1.12 | 1.16 | 1.21 |
| 10 | 1.10 | 1.12 | 1.14 |
| 15 | 1.04 | 1.08 | 1.11 |
| 20 | 1.08 | 1.11 | 1.13 |
| 30 | 1.07 | 1.11 | 1.13 |
| 45 | 1.04 | 1.04 | 1.01 |
| 60 | 1.04 | 1.01 | 1.01 | swelled after being transferred to sodium citrate and later during the storage in PBS. At higher reaction time, the capsule swelling was negligible—even a slight shrinking was observed.

FIG. 5 shows that reaction time has a great impact on the thickness of the capsular membrane, a property which determines finally capsule mechanical stability. For a given capsule size, the mechanical strength increases proportionally with the membrane thickness and can be orders of magnitude greater than that of the sodium alginate/poly(L-lysine) (SA/PLL/SA) microcapsules (data not shown). FIG. 5 also shows that initial membrane thickness decreases as the capsules are treated with the chelating agent, and this process continues in PBS. In addition, the formation of a thin distinct layer on the inside of the capsular membrane was observed after a few hours of storage in PBS.

EXAMPLE 11

Mechanical Strength

Figure 6:
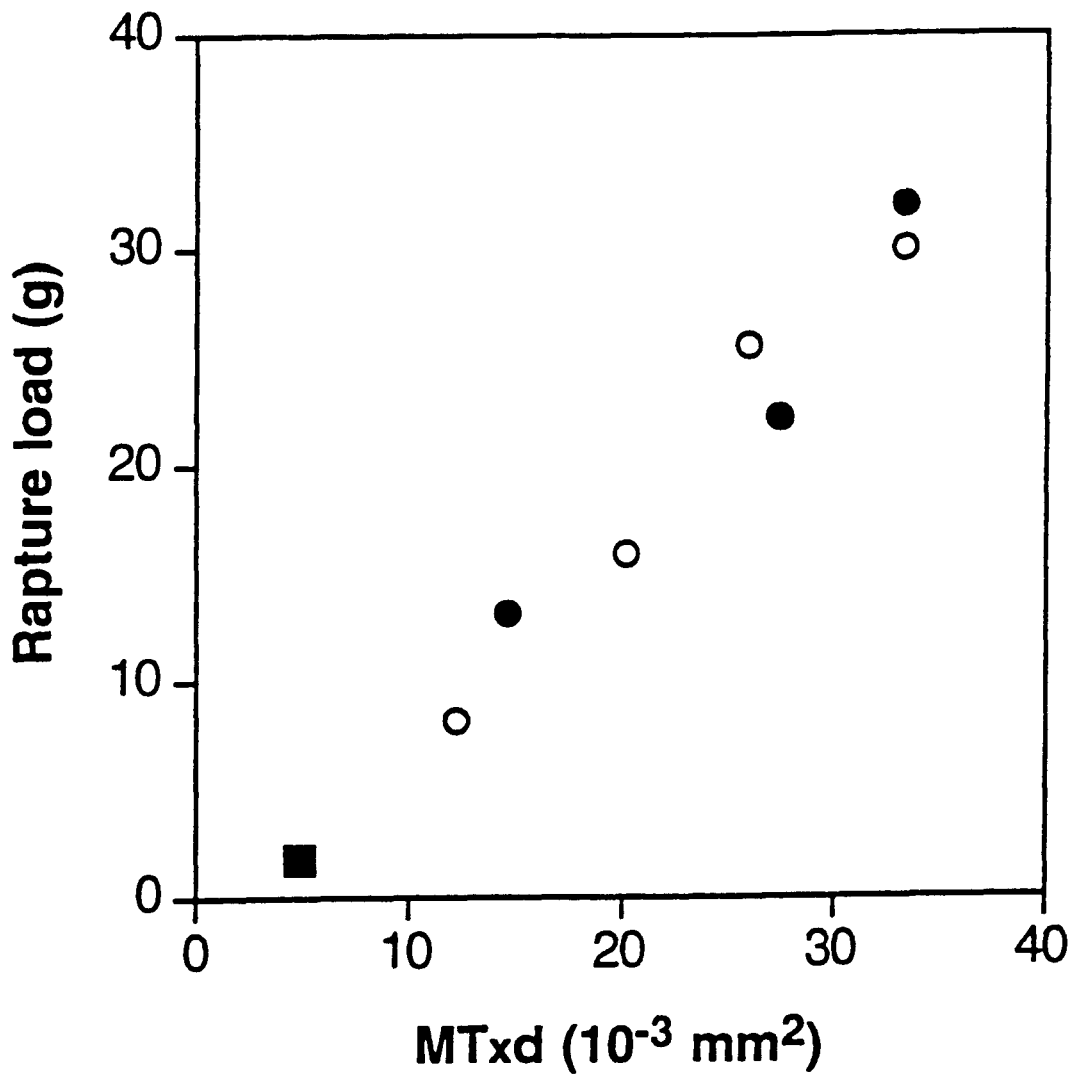
FIG. 6 shows that capsule mechanical stability is greatly increased. Mechanical burst strength of capsules as a function of wall thickness was measured by applying an uniaxial load. The solid square is the mechanical burst strength of sodium alginate-poly-(L-Lysine) SA/PLL capsules that were produced (ref. 37). The circles are the mechanical burst strength of SA/CS/PMCG capsules. The solid circle is the mechanical strength of 0.6% CS-0.6% Alginate capsules, and the open circle is 0.9% CS-0.9% Alginate capsules. MT=membrane thickness, d=diameter.

The mechanical strength of capsules was measured by placing an increasing uniaxial load on the capsule until the capsule burst. The capsule mechanical strength, a function of membrane thickness, can be adjusted from a fraction of a gram to tens of gram load to meet the needs of transplantation without altering the permeability of the capsule. FIG. 6 is a plot of the rupture load versus the product of membrane thickness and capsule size and demonstrates that the capsule of the present invention has much greater flexibility in mechanical strength than capsules formulated with the widely-used sodium alginate/polylysine system. The slope of the curve represents the rupture stress and thereby indirectly the inherent strength of the capsular membrane (ref. 34).

EXAMPLE 12

Diffusion Characteristics of Microcapsules

Measurement of capsule permeability was performed by utilizing two complementary methods: 1) size exclusion chromatography (SEC) with dextran molecular weight standards (ref. 35); and 2) a newly-developed method to assess permeability of a series of biologically-relevant proteins using encapsulated protein A-sepharose (PAS). By manipulating component concentration to control capsule permeability and using the above-mentioned methodologies to measure permeability, a series of capsules with a range of permeabilities (40 kDa–230 kDa, based on dextran exclusion measurement) was developed and characterized.

Figure 7:
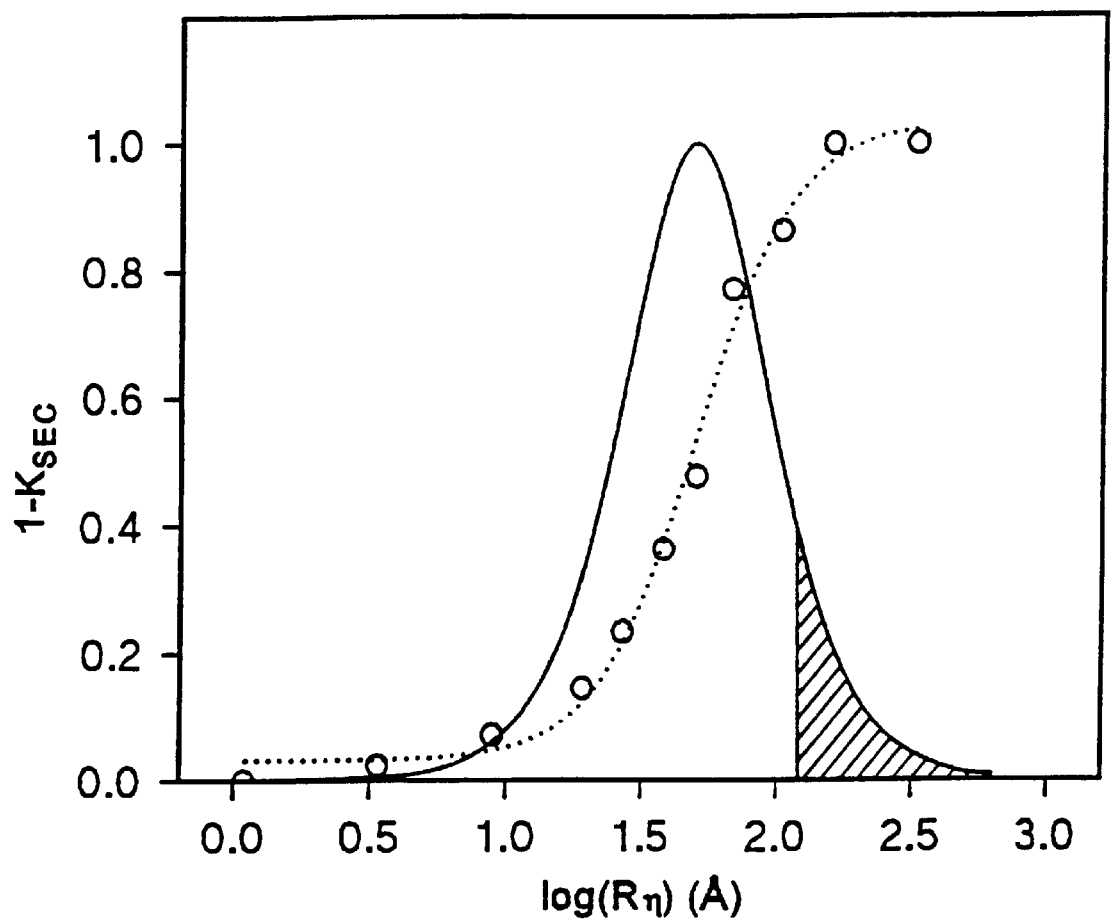
FIG. 7 shows the pore size distribution of capsular membranes of the present invention. Apparent pore size distribution (PSD) of $SA/CS/PMCG/CaCl_2/NaCl$ microcapsules was estimated based on dextran viscosity radius $R_n$. The cumulative PSD (dotted line) and differential PSD (solid line) are shown. The SA/CS/PMCG capsules were prepared from the mixture of 0.6% SA and 0.6% CS; the polycation solution contained 1.8% PMCG, 1% $CaCl_2$ and 0.9% NaCl with a one minute reaction time. The exclusion limit of this capsule, determined by SEC with dextran standards, was 230 kDa (ref. 35).

The apparent pore size of the capsular membrane was determined by size exclusion chromatography (SEC) which measured the exclusion of dextran solutes from the column packed with microcapsule (ref. 35). Using neutral polysaccharide molecular weight standards makes it possible to evaluate membrane properties under conditions where solute diffusion is controlled by its molecular dimension only. Based on the measured values of solute size exclusion coefficients ($K_{SEC}$) and known size of solute molecules, one can estimate the membrane pore size distribution (PSD) (FIG. 7). The differential PSD calculated for the microcapsules with 230 kDa exclusion limit showed a maximum at a viscosity radius $R_\eta$ equal to 50 Å. As determined from molecular weight calibration, the capsular membrane excluded dextran molecules with molecular weight above 230 kDa which corresponds to $R_\eta \geq 117$ Å (shaded area in FIG. 7).

Figure 8:
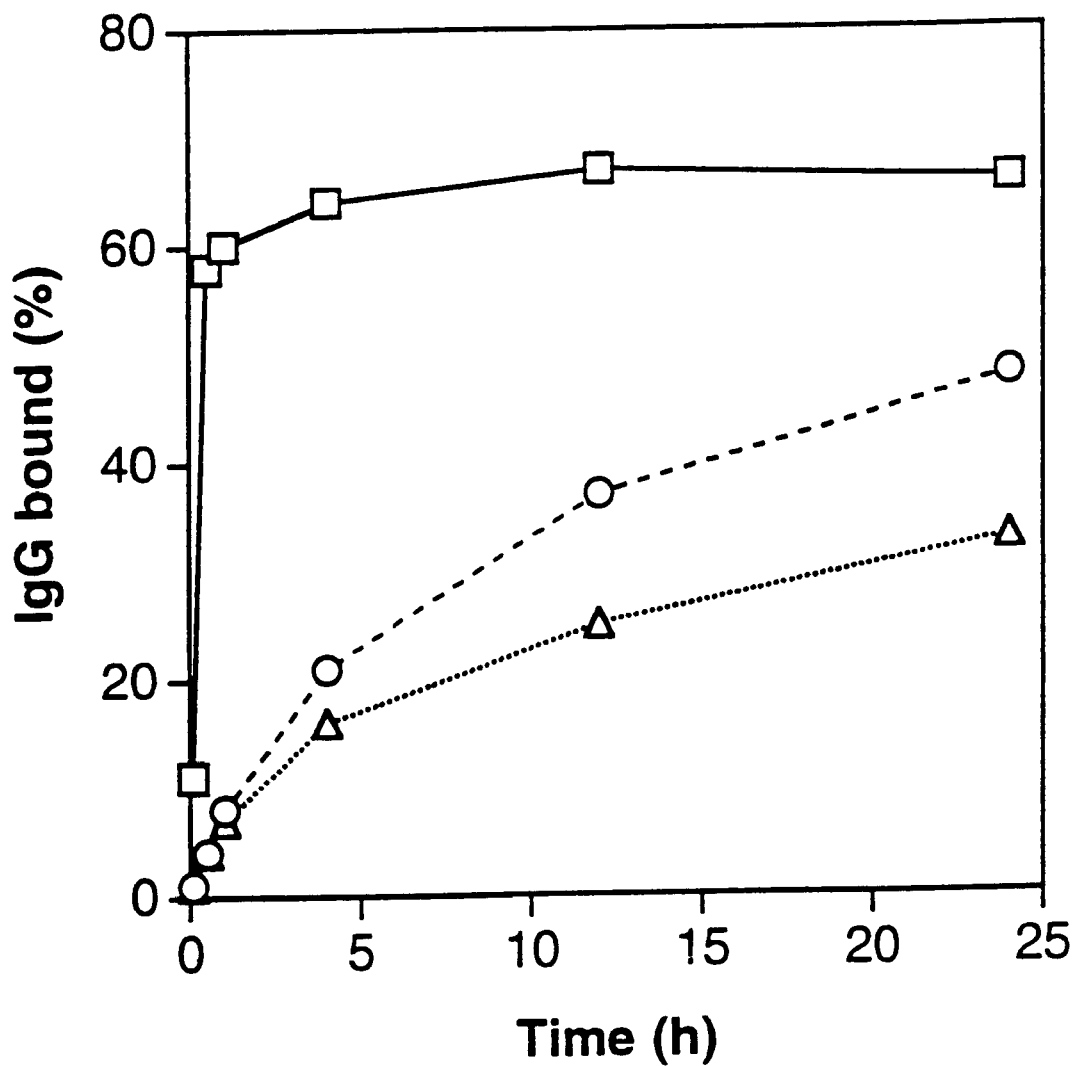
FIG. 8 shows capsule permeability to IgG. Time course of rabbit anti-mouse IgG-$^{125}$ binding to free and encapsulated protein-A sepharose (capsules with 230 kDa exclusion limit) are shown. Symbols: 18 μL of free protein-A sepharose gel (square), capsules loaded with 18 μL of protein-A sepharose gel (circle), empty capsules (triangle).

To assess capsule permeability to immunologically-relevant proteins, a new method involving encapsulated protein A-sepharose (PAS) was developed. IgG readily entered capsules with the 230 kDa exclusion limit (FIG. 8). The 110 kDa capsule, but not the 40 kDa, was permeable to IgG (data not shown). The SA/PLL capsules used by many have an exclusion limit of 100 kDa based on dextran measurements (ref. 35), which corresponds to a $R_\eta$ of 78 Å. It is noteworthy that the molecular size of IgG reported (ref. 36) is 52 Å and thus according to the calculated PSD in FIG. 7, the passage of IgG across the capsular membrane with 230 kDa exclusion limit would be expected. Even though IgG enters the capsules, islet destruction does not occur in vivo, presumably because entry of complement (required for cell lysis by IgG) would be prevented (based on capsule PSD and predicted size of complement).

Figure 9:
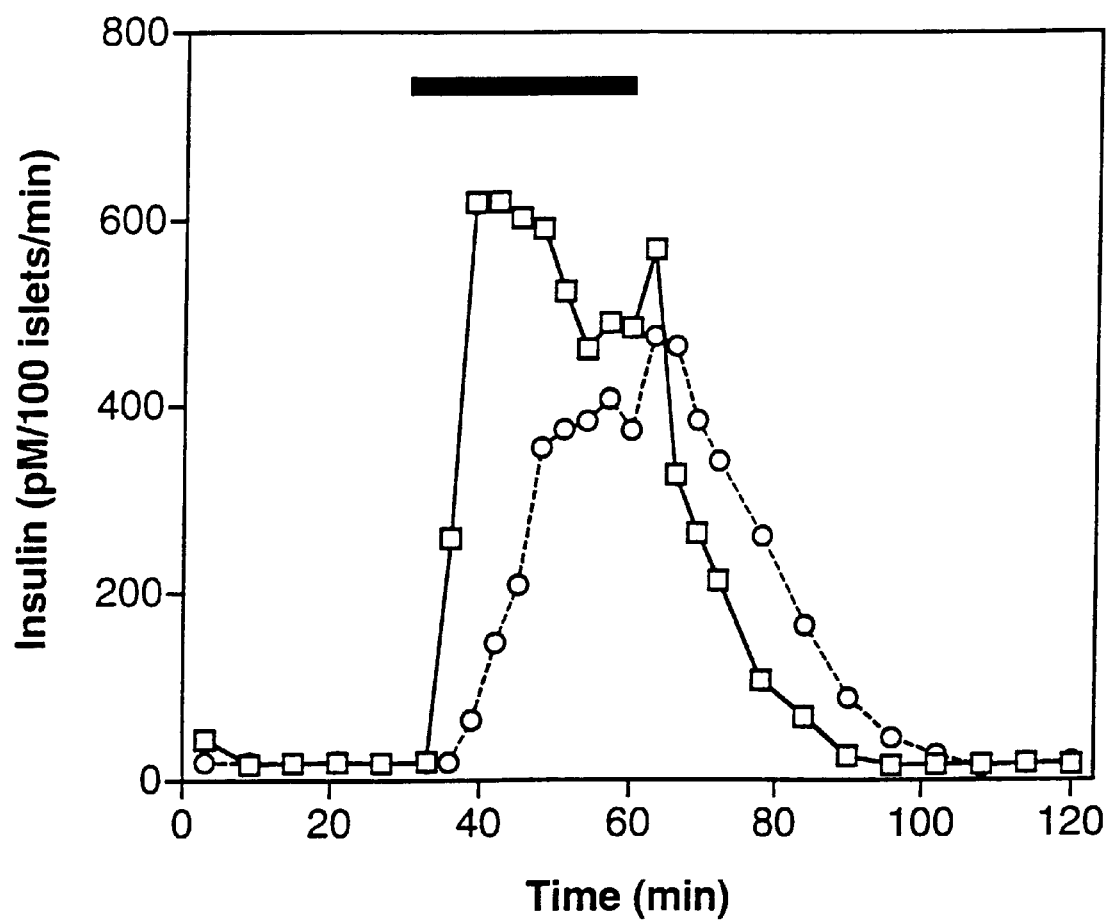
FIG. 9 shows insulin secretion by encapsulated pancreatic islets. Insulin response of islets in response to the glucose challenge as a function of time was measured in a cell perifusion system. Free and encapsulated islets (800 μm capsule diameter, 100 μm membrane thickness, exclusion limit 230 kDa) were cultured at 24° C. in RPMI 1640 medium supplemented with 5 mM glucose and 10% fetal calf serum for 24 hours prior to the perifusion. Results from experiments with unencapsulated islets (squares) and encapsulated islets (circles) are shown. The black bar at the top of the graph shows the stimulation period with 20 mM glucose and 0.045 mM IBMX.

Viability and function of rat pancreatic islets enclosed in the capsules with 230 kDa exclusion limit was tested in vitro (FIG. 9). Using a cell perifusion apparatus, glucose-stimulated insulin secretion by rat pancreatic islets, enclosed within capsules with a dextran exclusion limit of 230 kDa, was well-preserved barring a slight delay in comparison with unencapsulated islets (FIG. 9). Islets enclosed in capsules with differing wall thicknesses, but the same 230 kDa exclusion limit, showed a similar insulin response.

EXAMPLE 13

Animal Trials: Empty Capsules

Figure 10A:
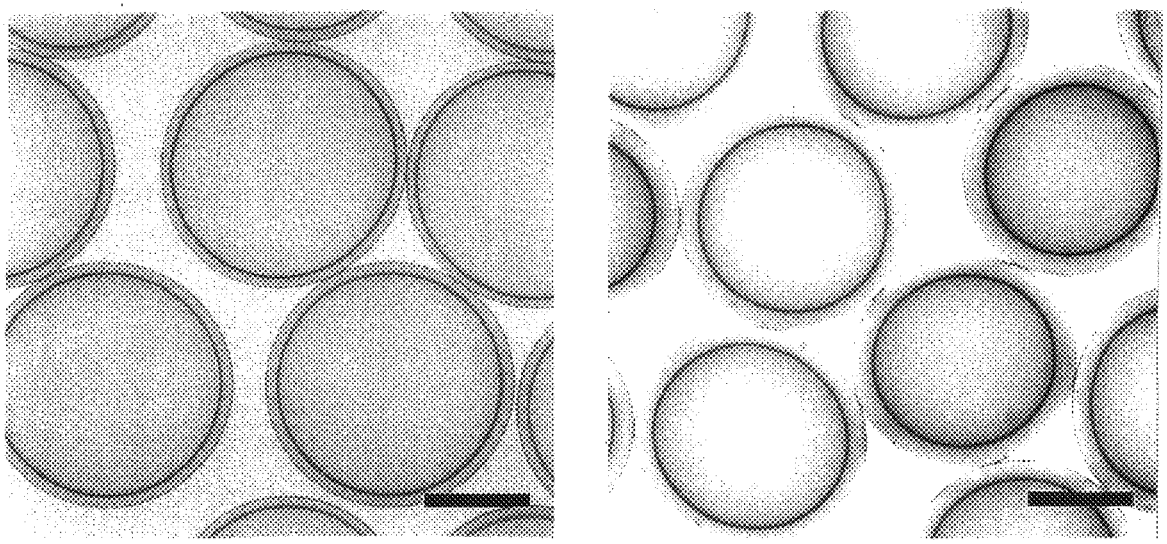
FIG. 10A shows capsules prior to transplantation (black bar is 340 μm) and FIG. 10B shows capsules retrieved from normal mice (black bar is 340 μm).
Figure 10B:
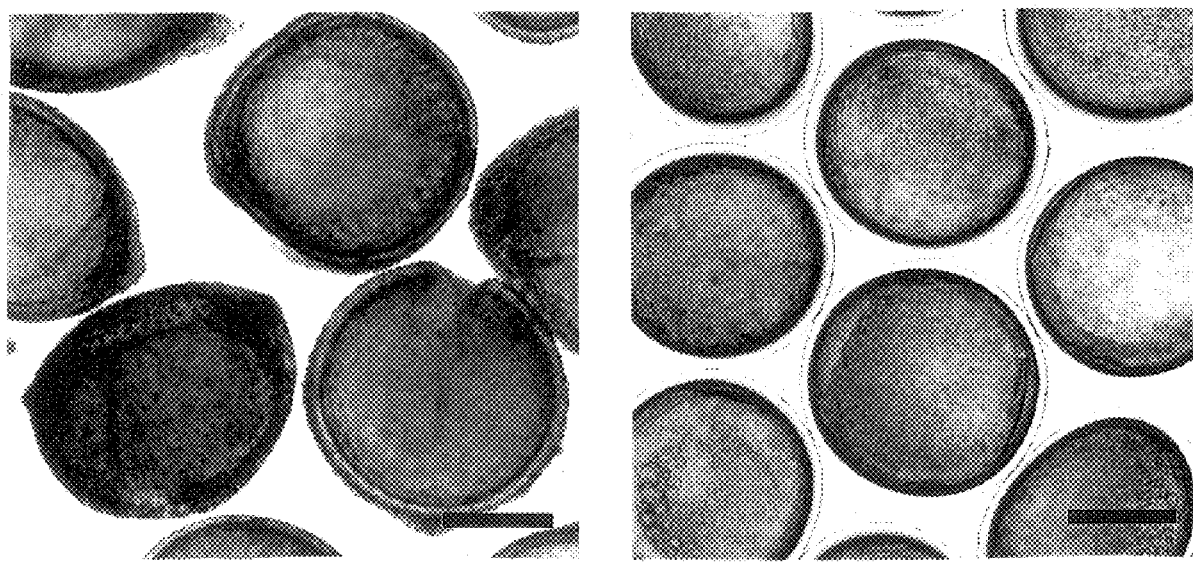

Prior to transplantation of encapsulated islets into animals, extensive biocompatibility testing of empty capsules was performed. Capsules were transplanted into the peritoneal cavity of healthy mice to study biocompatibility and later retrieved to study the tissue reaction and fibrosis on the capsule surface. The experimental results were surprising in that capsules similar in physical appearance, mechanical strength, and permeability, exhibited drastic differences in biocompatibility. For example, two capsules, which were prepared under identical processing steps and differed only in PMCG concentration—1% PMCG versus 1.8%—demonstrated a remarkable difference in the ability to stimulate fibrosis on the capsule surface (FIG. 10). These data suggest that a narrow window of operation parameters exist, both in chemistry and capsule processing, and that minor variations may have strong impact on biocompatibility.

EXAMPLE 14

Diabetes Reversal

Figure 11A:
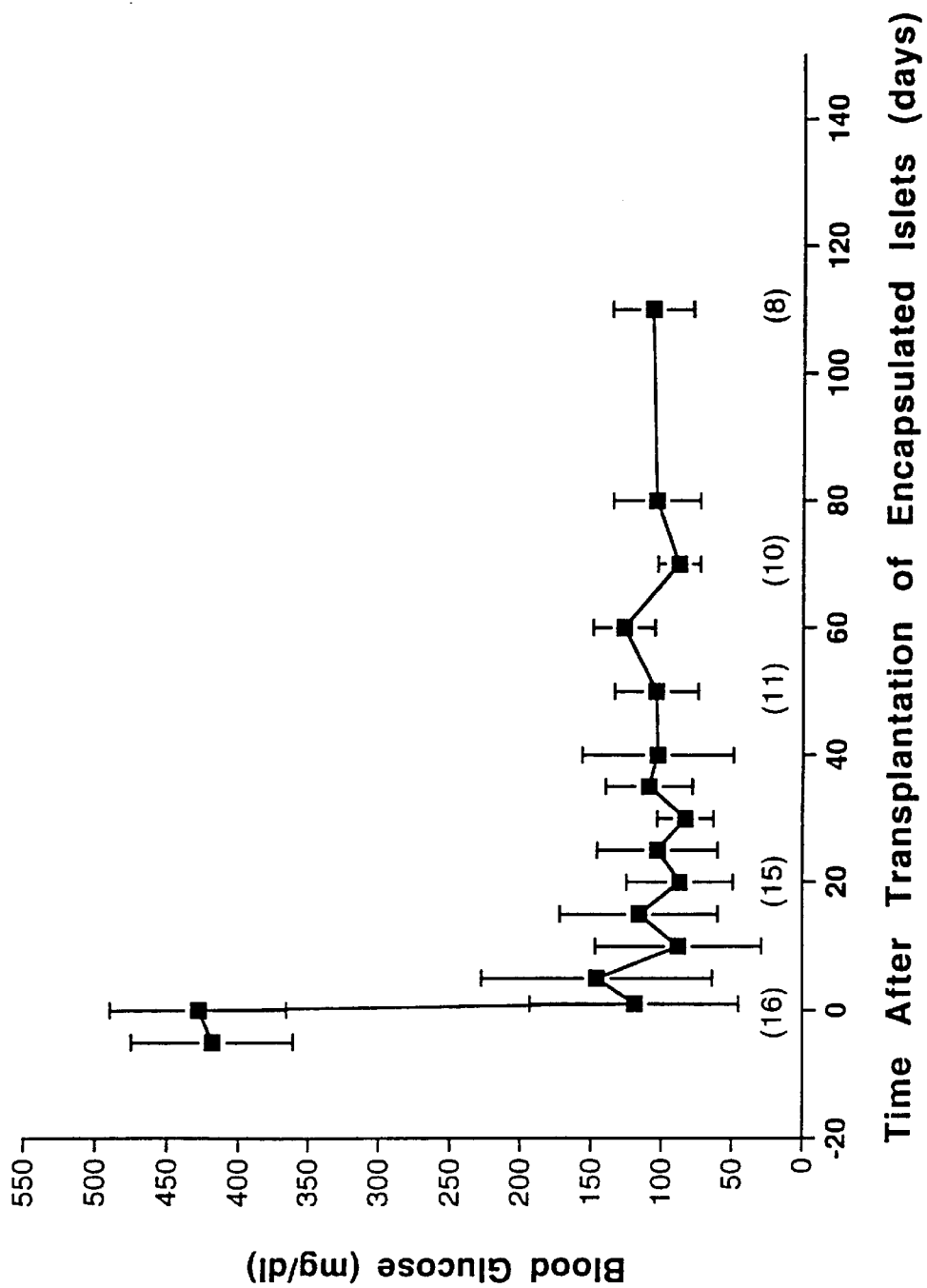
FIG. 11A: Approximately 1000 encapsulated rat islets (0.8 mm capsule with 0.1 mm wall thickness and exclusion limit of 230 kDa) were transplanted intraperitoneally into diabetic C57/B16 mice (strepzotocin-induced). The mean and standard deviation of blood sugars of non-diabetic animals (measured using a One-touch glucometer) were plotted against the number of days following transplantation. Of the sixteen diabetic mice which received transplants, the number of non-diabetic animals at selected time points is shown in parentheses. Of the eight animals with normal blood sugars 110 days following transplantation, two later became diabetic while six were still normoglycemic 300 days following transplantation.
Figure 11B:
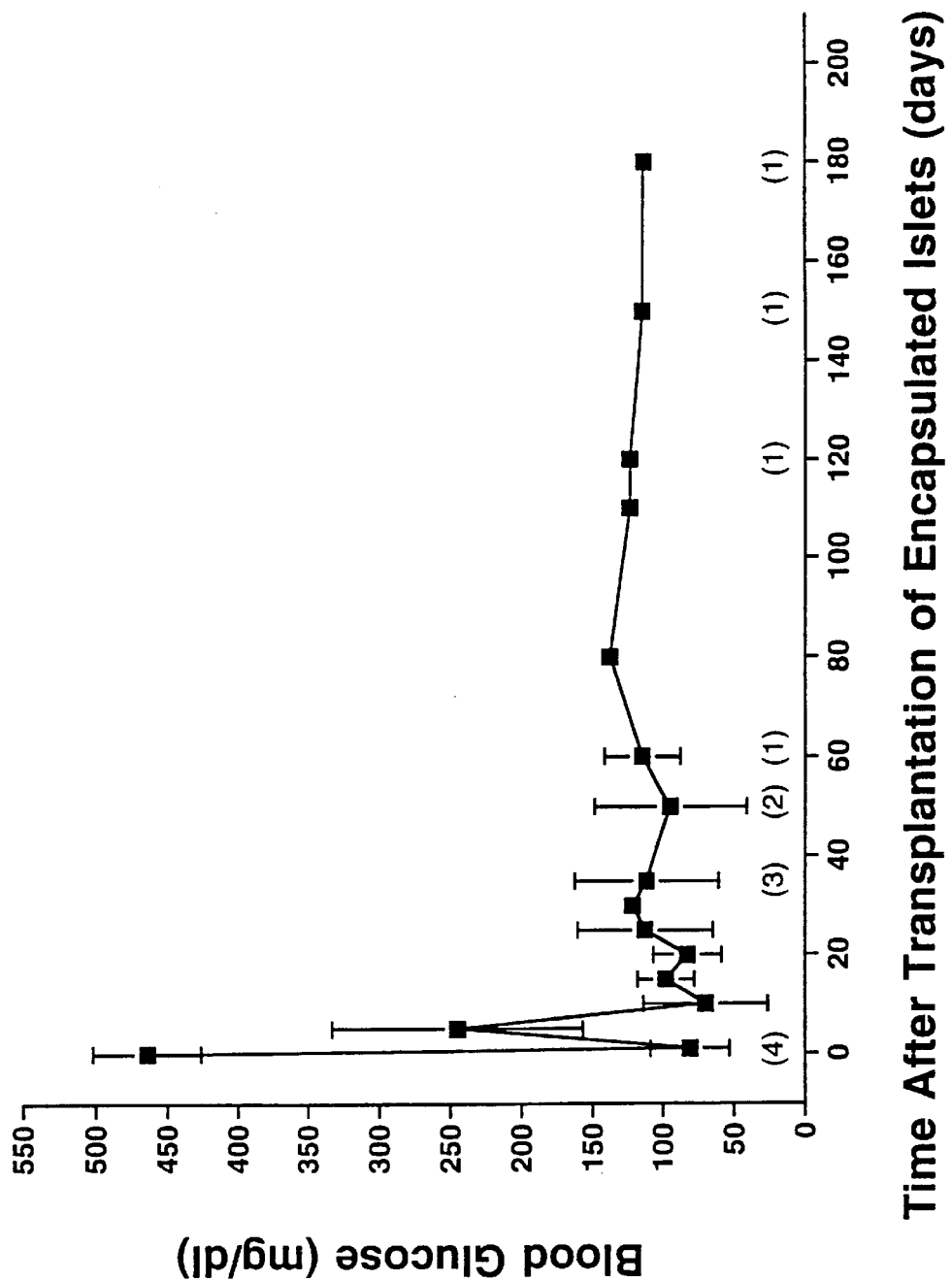
FIG. 11B: Encapsulated rat islets were transplanted into the peritoneal cavity of female NOD mice which had developed spontaneous diabetes by the age of 20 weeks. Of the four diabetic mice that received transplants, the number of non-diabetic animals at selected time points is shown in parentheses.
Figure 12A:
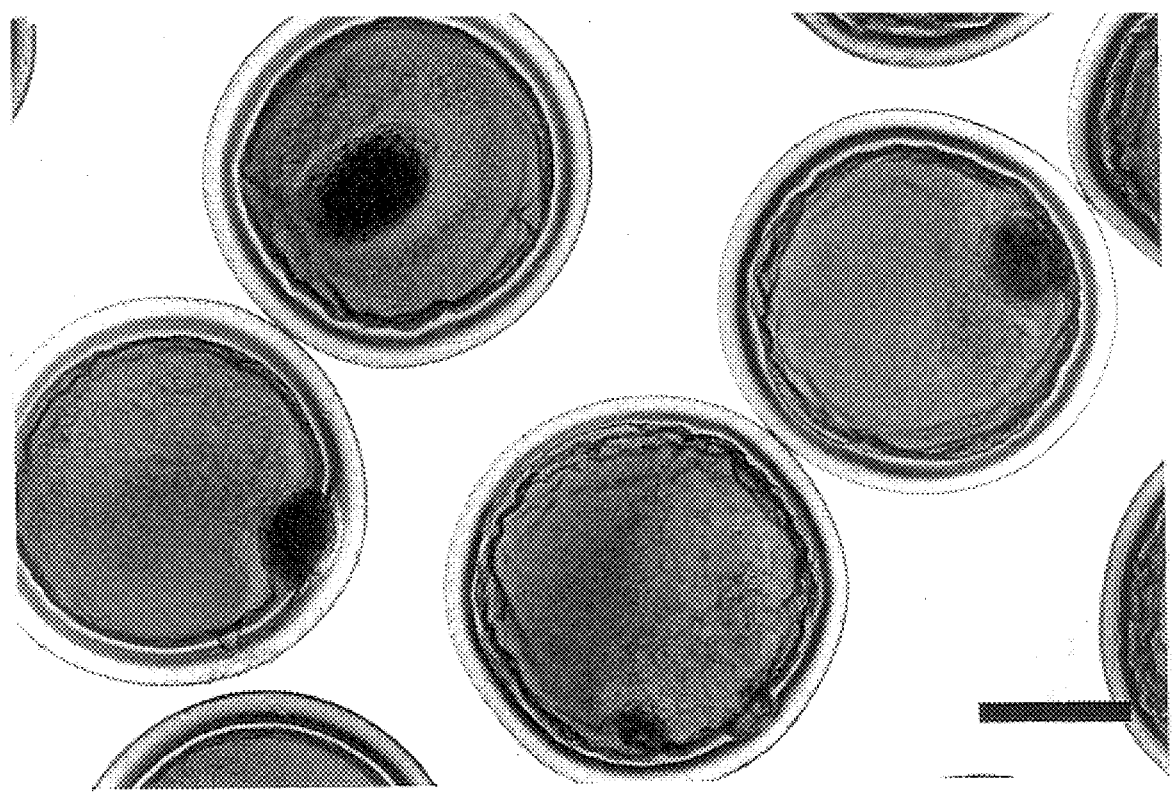
FIG. 12A: the viability of encapsulated islets retrieved one year following transplantation into diabetic C57/B16 mice was assessed in the cell perifusion apparatus as described in FIG. 4. The bar at the top shows the stimulation period with 20 mM glucose and 0.045 mM IBMX. For comparison, insulin secretion of unencapsulated islets (squares), freshly encapsulated islets (diamonds), and retrieved encapsulated islets (circles) is shown.
Figure 12B:
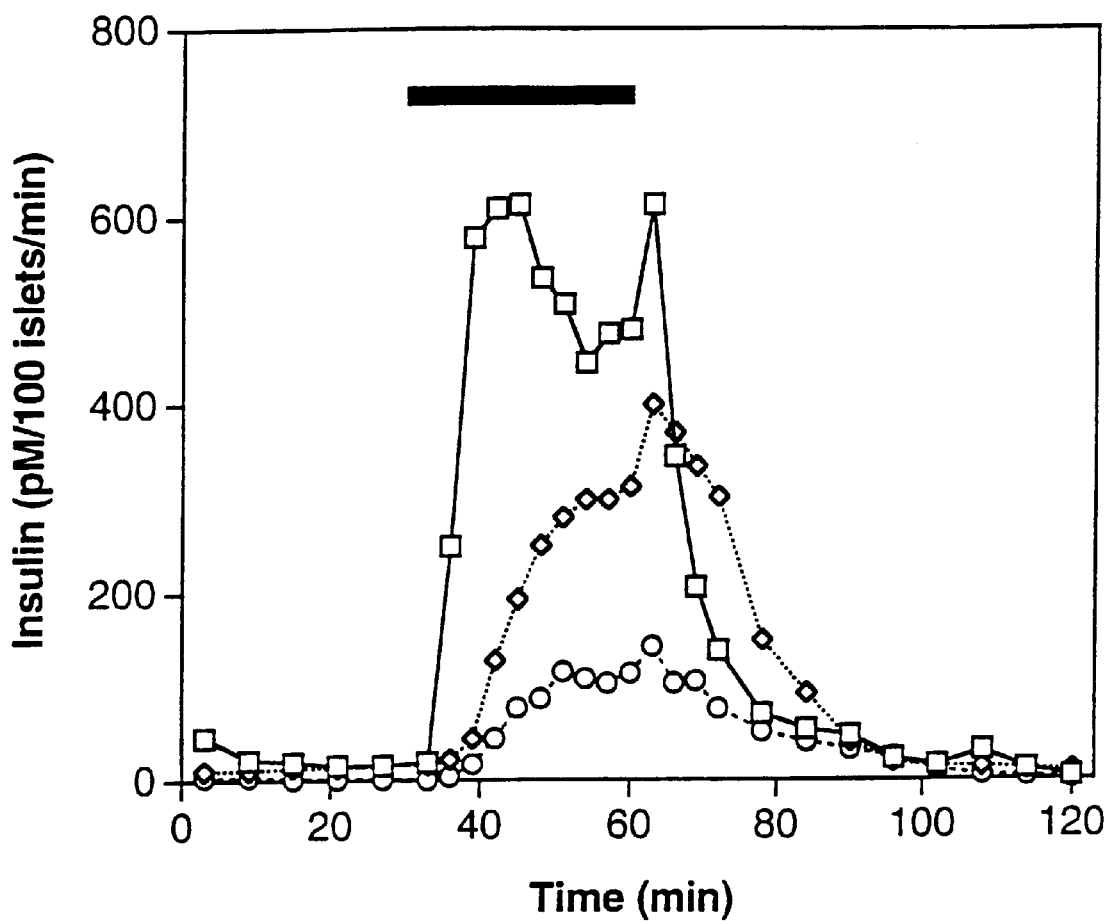
FIG. 12B: retrieved encapsulated islets were photographed. The black bar is equal to 340 mm.

Encapsulated rat islets readily reversed chemically-induced diabetes in mice (strepzotocin-induced) and islet function was maintained for at least 4–6 months (FIG. 11A). Similar studies were performed with diabetic NOD female mice and diabetes was reversed for up to 180 days (FIG. 11B). The encapsulated islets, transplanted into the peritoneal cavity, are free-floating, quite biocompatible and show no significant fibrosis or tissue reaction (FIG. 12). Encapsulated islets have long-term function as assessed by their ability to secrete insulin following glucose stimulation (FIG. 12A). The eventual decrease in effectiveness of encapsulated islets transplanted into animals with chemically-induced diabetes did not result from capsule rupture or from an immune attack. Capsules retrieved from those animals were free-floating and their surface was free of fibrosis. Thus, the decrease likely resulted from islet death within the capsule, possibly from a nutrient deficiency or from islet toxicity because of soluble immune factors (cytokines). In contrast, the decrease in effectiveness of encapsulated islets transplanted into NOD mice may have resulted from an immune or autoimmune attack. Capsules ultimately retrieved from those animals were clumped and demonstrated marked fibrosis around the capsule surface.

The following references were cited herein:
1. Colton, C. K. & Avgoustiniatos, E. SECONDS. 1991. Bioengineering in development of the hybrid artificial pancreas. *Journal of Biomechanical Engineering* 113, 152–170.
2. Lanza, R. P., Sullivan, SECONDS. J. & Chick, W. L. 1992. Islet Transplantation with Immunoisolation. *Diabetes* 41, 1503–1510.
3. Chang, T. M. 1992. Hybrid artificial cells: microencapsulation of living cells. *ASAIO Journal* 38, 128–130.
4. Maki, T., Mullon, C. J., Solomon, B. A. & Monaco, A. P. 1995. Novel delivery of pancreatic islet cells to treat insulin-dependent diabetes mellitus. *Clinical Pharmacokinetics* 28, 471–482.
5. Reach, G. 1994. Bioartificial pancreas. *Transplantation Proceedings* 26, 397–398.
6. Lacy, P. E. 1995. Treating diabetes with transplanted cells. *Scientific American* 273, 50–58.
7. Ricordi, C. *Pancreatic islet cell transplantation* (R.G. Landes Company, Austin, 1992).
8. Lanza, R. P., Kuehtreiber, W. M., Ecker, D., Staruk, J. E. & Chick, W. L. 1995. Xenotransplantation of porcine and bovine islets without immunosuppression using uncoated alginate microspheres. *Transplantation* 59, 1377–1384.
9. Lanza, R. P., Beyer, A. M. & Chick, W. L. 1994. Xenogenic humoral responses to islets transplanted in biohybrid diffusion chambers. *Transplantation* 57, 1371–1375.
10. O'Shea, G. M. & Sun, A. M. 1986. Encapsulation of rat islets of Langerhans prolongs xenograft survival in diabetic mice. *Diabetes* 35, 943–946.
11. Lanza, R. P., Butler, D. H., Borland, K. M., Staruk, J. E., Faustman, D. L., Solomon, B. A., et al. 1991. Xenotransplantation of canine, bovine, and porcine islets in diabetic rats without immunosuppression. *Proceedings of the National Academy of Sciences of the United States of America* 88, 11100–11104.
12. Lum, Z. P., Tai, I. T., Krestow, M., Norton, J., Vacek, I. & Sun, A. M. 1991. Prolonged reversal of diabetic state in NOD mice by xenografts of microencapsulated rat islets. *Diabetes* 40, 1511–1516.
13. Soon-Shiong, P., Feldman, E., Nelson, R., Heintz, R., Yao, Q., Yao, Z., et al. 1993. Long-term reversal of diabetes by the injection of immunoprotected islets. *Proceedings of the National Academy of Sciences of the United States of America* 90, 5843–5847.
14. Soon-Shiong, P., Heintz, R. E., Merideth, N., Yao, Q. X., Yao, Z., Zheng, T., et al. 1994. Insulin independence in a type 1 diabetic patient after encapsulated islet transplantation. *Lancet* 343, 950–951.
15. Scharp, D. W., Swanson, C. J., Olack, B. J., Latta, P. P., Hegre, O. D., Doherty, E. J., et al. 1994. Protection of encapsulated human islets implanted without immunosuppression in patients with type I or type II diabetes and in nondiabetic control subjects. *Diabetes* 43, 1167–1170.
16. Weber, C., Krekun, SECONDS., Koschitzky, T., Zabinski, SECONDS., D'Agati, V., Hardy, M., et al. 1991. Prolonged functional survival of rat-to-NOD mouse islet xenografts by ultraviolet-B (UV-B) irradiation plus microencapsulation of donor islets. *Transplantation Proceedings* 23, 764–766.
17. Calafiore, R., Basta, G., Osticioli, L., Luca, G., Tortoioli, C. & Brunetti, P. 1996. Coherent microcapsules for pancreatic islet transplantation: a new approach for bioartificial pancreas. *Transplantation Proceedings* 28, 812–813.
18. Lim, F. & Sun, A. M. 1980. Microencapsulated islets as bioartificial endocrine pancreas. *Science* 210, 908–910.
19. Goosen, M. F. A. in *Immunoisolation of Pancreatic Islets* (eds Lanza, R. P. & Chick, W. L.) 21–44 (R.G. Landes Company, Autin, 1994).
20. De Vos, P., Wolters, G. H. J., Fritschy, W. M. & van Schilfgaarde, R. 1993. Obstacles in the application of microencapsulation in islet transplantation. *International Journal of Artifical Organs* 16, 205–212.
21. Goosen, M. F. A., O'Shea, G., Gharapetian, H. M., Chou, SECONDS. & Sun, A. M. 1985. Optimization of Microencapsulation Parameters: Semipermeable Microcapsules as a Bioartificial Pancreas. *Biotechnology and Bioengineering* 27, 146–150.
22. Crooks, C. A., Douglas, J. A., Broughton, R. L. & Sefton, M. V. 1990. Microencapsulation of mammalian cells in a HEMA-MMA copolymer: effects on capsule morphology and permeability. *Journal of Biomedical Materials Research* 24, 1241–1262.
23. Wang, T., Lacik, I., Brissova, M., Anilkumar, A. V., Prokop, A., Hunkeler, D., Green, R., Shahrokhi, K., Powers, A.C. 1997. An Encapsulation System for the Immunoisolation of Pancreatic islets. *Nature-Biotechnology.*
24. Kendall, J. M., Lee, M. C. & Wang, T. G. 1982. Fluid and chemical dynamics relating to encapsulation technology. *Journal of Vacuum Science Technology* 20, 1091.
25. Kendall, J. M. 1986. Experiments on annular liquid jet instability and on the formation of liquid shells. *Physical Fluids* 29, 2086–2094.
26. Lee, C. P. & Wang, T. G. 1988. The centering dynamics of a thin liquid shell in capillary oscillations. *Journal of Fluid Mechanics* 188, 411–435.
27. Lin, K. C. & Wang, T. G. 1992. A novel method for producing microspheres with semipermeabile polymer membranes. *AIAA* 92–0118,
28. Kendall, J. M., Chang, M. & Wang, T. G. 1988. Fluid and chemical dynamics relating to encapsulation technology. *American Institute of Physics Proceedings* 197, 487–495.
29. Kelco, Division of Merck & Co., *Alginate Products for Scientific Water Control,* 3rd Edition.
30. A. Martinsen, G. Skjåk-Bræk, and O. Smidsrød, Alginate as immobilization material: I. Correlation between chemical and physical properties of alginate gel beads, *Biotechnol. Bioeng.,* 33, 79–89 (1989).
31. O SmidsrØd, Solution properties of alginate, *Carbohyd. Res.,* 13, 359–372 (1970).
32. K Kishino, T. Kawai, T. Nose, M. Saitoh, and K. Kamide, Dilute solution properties of sodium cellulose disulfate, *Eur. Polym. J.,* 17, 623–630 (1981).
33. J. J. Waldmann, Compositions of inorganic-organic alloy with high nitrogen content polymers and their manufacture, U.S. Pat. No. 4,891,422 (1990).
34. Lardner, T. & Pujara, P. 1980. Compression of spherical cells. *Mechanics Today* 161–176.
35. Brissová, M., Lacík, I., Powers, A. C. & Wang, T. G. 1996. Evaluation of microcapsule permeability via insverse size exclusion chromatography. *Analytical Biochemistry* 242, 104–111.
36. Nave, R., Weber, K. & Potschka, M. 1993. Universal calibration of size-exclusion chromatography for proteins in guanidinium hydrochoride including the high-molecular-mass proteins titin and nebulin. *Journal of Chromatography* A654, 229–246.
37. Sun, Y. L., Ma, X., Zhou, D., Vacek, I. & Sun, A. M. 1993. Porcine pancreatic islets: isolation, microencapsulation, and xenotransplantation. *Artificial Organs* 17, 727–733.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition of matter for the encapsulation of cells comprising high viscosity sodium alginate, cellulose sulfate, and a multi-component polycation, wherein said polycation is selected from the group consisting of poly(methylene-co-guanidine)hydrochloride, calcium chloride and sodium chloride.

2. The composition of matter of claim 1, wherein said high viscosity sodium alginate and said cellulose sulfate are in a ratio of approximately 1:1.

3. The composition of matter of claim 1, wherein said high viscosity sodium alginate and said cellulose sulfate are at a total concentration of 0.8 wt-% to 2.4 wt-%.

4. The composition of matter of claim 3, wherein said high viscosity sodium alginate and said cellulose sulfate are at a total concentration of 1.0 wt-% to 1.2 wt-%.

5. The composition of matter of claim 1, wherein each component of said multi-component polycation is at a concentration of 0.5 wt-% to 5.0 wt-%.

6. The composition of matter of claim 5, wherein each component of said multi-component polycation is at a concentration of 0.8 wt-% to 2.8 wt-%.

7. The composition of matter of claim 1 wherein said poly(methylene-co-guanidine)hydrochloride is at a concentration of about 0.5 wt-% to 5.0 wt-%, calcium chloride is at a concentration of about 0.5 wt-% to 5.0 wt-%, and sodium chloride is at a concentration of about 0.5 wt-% to 5.0 wt-%.

8. The composition of matter of claim 7, wherein said poly(methylene-co-guanidine)hydrochloride is at a concentration of about 1.8 wt-%., calcium chloride is at a concentration of about 1.0 wt-%, and sodium chloride is at a concentration of about 0.9 wt-%.

9. The composition of claim 1 wherein the microcapsule formed by said encapsulation has a diameter of from about 0.5 mm to about 2.0 mm.

* * * * *

UNITED STATES PATENT AND TRADEMARK OFFICE
CERTIFICATE OF CORRECTION

PATENT NO.   : 5,997,900
DATED        : December 7, 1999
INVENTOR(S)  : Taylor G. Wang, et al It is certified that error appears in the above-identified patent and that said Letters Patent is hereby corrected as shown below:

On the title page under item [76] Inventors, "Anikumar" should read --Anilkumar --.

Signed and Sealed this

Twenty-fourth Day of April, 2001

Attest:

NICHOLAS P. GODICI

Attesting Officer

Acting Director of the United States Patent and Trademark Office